United States Patent [19]

Wilson et al.

[11] Patent Number: 5,342,604

[45] Date of Patent: Aug. 30, 1994

[54] COMPLEXES POSSESSING ORTHO LIGATING FUNCTIONALITY

[75] Inventors: David A. Wilson, Richwood; Joseph R. Garlich; R. Keith Frank, both of Lake Jackson; Kenneth McMillan, Richwood; Jaime Simon, Angleton, all of Tex.

[73] Assignee: The Dow Chemical Company, Midland, Mich.

[21] Appl. No.: 900,808

[22] Filed: Jun. 17, 1992

Related U.S. Application Data

[63] Continuation-in-part of Ser. No. 421,452, Oct. 13, 1989, abandoned, which is a continuation-in-part of Ser. No. 265,158, Oct. 31, 1988, abandoned.

[51] Int. Cl.$^5$ .................. A61K 43/00; A61K 49/02; C07F 3/00; C07F 5/00
[52] U.S. Cl. ........................... 424/1.65; 534/10
[58] Field of Search .................. 424/1.65; 534/10, 14, 534/16; 562/443

[56] References Cited

U.S. PATENT DOCUMENTS

| | | | |
|---|---|---|---|
| 2,763,680 | 9/1956 | Sallmann | 562/52 |
| 3,189,630 | 6/1965 | Smutny | 534/16 |
| 3,312,552 | 4/1967 | Muller-Hardorff et al. | 430/634 |
| 4,046,793 | 9/1977 | Baccini et al. | 556/148 |
| 4,088,747 | 5/1978 | Hunt et al. | 424/1.1 |
| 4,091,088 | 5/1978 | Hunt et al. | 424/1.1 |
| 4,622,420 | 11/1986 | Meares et al. | 562/443 |
| 4,647,447 | 3/1987 | Gries et al. | 573/184 |
| 4,801,722 | 1/1989 | Hinshaw et al. | 562/441 X |
| 5,124,471 | 6/1992 | Gansow et al. | 562/443 X |

FOREIGN PATENT DOCUMENTS

| | | |
|---|---|---|
| 0068875 | 1/1983 | European Pat. Off. . |
| 0230893 | 8/1987 | European Pat. Off. . |
| 2238699 | 2/1975 | France . |
| 353747 | 6/1961 | Switzerland . |
| 8801618 | 3/1988 | World Int. Prop. O. . |

OTHER PUBLICATIONS

Chemical Abstracts, vol. 86, No. 19, May 9, 1977, p. 524, Abstract No. 139627d, Columbus, Ohio.
Patrick L. Carney, et al., 3rd, International Conf. on Monoclonal Antibodies, Feb. 4–6, 1988.
Arthur E. Martell, et al., Inorganica Chemica Acta 138, 215–230 (1987).

Primary Examiner—Robert L. Stoll
Assistant Examiner—John M. Covert
Attorney, Agent, or Firm—Karen L. Kimble

[57] ABSTRACT

A group of functionalized amine chelants having ortho ligating functionality that form complexes with rare-earth type metal ions are disclosed. The chelants possess the general formula

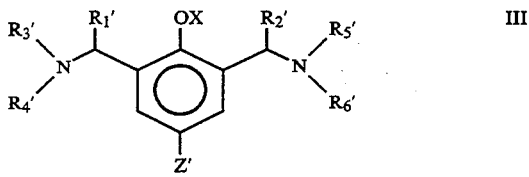

wherein $R'^1$, $R'^2$, $R'^3$, $R'^4$, $R'^5$ and $R'^6$, $Z'$ and $X$ are all defined in the specification. In addition certain of the chelant-radionuclide complexes can be effectively employed in compositions useful as therapeutic and/or diagnostic agents for calcific tumors and/or relief of bone pain.

8 Claims, No Drawings

COMPLEXES POSSESSING ORTHO LIGATING FUNCTIONALITY

CROSS REFERENCE TO RELATED APPLICATIONS

This application is a continuation-in-part of copending application U.S.S.N. 421,452, filed Oct. 13, 1989, which is a continuation-in-part of application U.S.S.N. 265,158, filed Oct. 31, 1988, now abanboned.

1. Field of the Invention

The present invention concerns chelants passessing ortho ligating fuctionality, complexes and conjugates thereof, processes for their preparation, formulations for their use and methods for their use in cancer diagnostics and/or therapy.

2. Background of the Invention

Functionalized chelants, or bifunctional coordinators, are known to be capable of being covalently attached to an antibody having specificity for cancer or tumor cell epitopes or antigens. Radionuclide complexes of such antibody/chelant conjugates are useful in diagnostic and/or therapeutic applications as a means of conveying the radionuclide to a cancer or tumor cell. See, for example, Meares et al., *Anal. Biochem.* 142, 68–78, (1984); and Krejcarek et al., *Biochem. and Biophys. Res. Comm.* 77, 581–585 (1977).

Aminocarboxylic acid chelating agents have been known and studied in the literature for several years. Typical of the aminocarboxylic acids are nitrilotriacetic acid (NTA), ethylenediaminetetraacetic acid (EDTA), hydroxyethylethylenediaminetriacetic acid (HEDTA), diethylenetriaminepentaacetic acid (DTPA) and trans-1,2-diaminocyclohexanetetraacetic acid (CDTA). Numerous bifunctional chelating agents based on aminocarboxylic acids have been proposed and prepared. For example the cyclic dianhydride of DTPA (Hnatowich et.al. *Science*, 220, 613–615, 1983; U.S. Pat. No. 4,479,930) and mixed carboxycarbonic anhydrides of DTPA (Gansow, U.S. Pat. Nos. 4,454,106 and 4,472,509; Krejcarek et al., *Biochem. and Biophys. Res. Comm.* 77, 581–585, 1977) have been reported in the literature. When the anhydrides are coupled to proteins the coupling proceeds via formation of an amide bond thus leaving four of the original five carboxymethyl groups on the diethylenetriamine (DETA) backbone (Hnatowich et al., *Int. J. Appl. Isot.* 33, 327–332, 1982). In addition, U.S. Pat. Nos. 4,432,907 and 4,352,751 disclose bifunctional chelating agents useful for binding metal ions to "organic species such as organic target molecules or antibodies." As in the above, coupling is obtained via an amide group through the utilization of diaminotetraacetic acid dianhydrides. Examples of anhydrides include dianhydrides of EDTA, CDTA, propylenediaminetetraacetic acid and phenylene 1,2-diaminetetraacetic acid. A recent U.S. Pat. No. 4,647,447 discloses several complex salts formed from the anion of a complexing acid for use in various diagnostic techniques. Conjugation via a carboxyl group of the complexing acid is taught which gives a linkáge through an amide bond.

Another class of bifunctional chelating agent based on aminocarboxylic acid functionality is also well documented in the literature. Thus, Sundberg et al. in the *J. of Med. Chem.* 17(12), 1304 (1974) discloses bifunctional analogs of EDTA. Representative of these compounds are 1-(p-nitrophenyl)ethylenediaminetetraacetic acid, 1-(p-aminophenyl)ethylenediaminetetraacetic acid, and 1-(p-benzenediazonium)ethylenediaminetetraacetic acid. Coupling to proteins through the para-substituent and the binding of radio-active metal ions to the chelating group is discussed. The compounds are also disclosed in *Biochem. Biophys. Res. Comm.* 75(1), 149 (1977) and in U.S. Pat. Nos. 3,994,966 and 4,043,998. It is important to note that attachment of the aromatic group to the EDTA structure is through a carbon of the ethylenediamine backbone. Optically active bifunctional chelating agents based on EDTA, HEDTA and DTPA are disclosed in U.S. Pat. No. 4,622,420. Also in this reference the attachment of the aminocarboxylic acid functionality to the rest of the bifunctional chelating molecule is through a carbon of the ethyleneamine backbone. In these compounds an alkylene group links the aromatic group (which contains the functionality needed for attachment to the protein) to the carbon of the polyamine which contains the chelating functionality. Other references to such compounds include Brechbiel et al. *Inorg. Chem.* 25, 2772–2781 (1986), U.S. Pat. No. 4,647,447 and a published PCT application having International Publication Number WO 86/06384. More recently, certain macrocyclic bifunctional chelating agents and the use of their copper chelate conjugates for diagnostic or therapeutic applications have been disclosed in U.S. Pat. No. 4,678,667. Attachment of the aminocarboxylic acid functionality to the rest of the bifunctional chelating molecule is through a ring carbon of the cyclic polyamine backbone. Thus, a linker, attached at one end to a ring carbon of the cyclic polyamine, is also attached at its other end to a functional group capable of reacting with the protein.

Another class of bifunctional chelating agent, also worthy of note, consists of compounds wherein the chelating moiety, i.e. the aminocarboxylic acid, of the molecule is attached through a nitrogen to the functional group of the molecule containing the moiety capable of reacting with the protein. As an example Mikola et al. in a published PCT application (International Publication Number WO 84/03698, published Sep. 27, 1984) disclose a bifunctional chelating agent prepared by reacting p-nitrobenzylbromide with DETA followed by reaction with bromoacetic acid to make the aminocarboxylic acid. The nitro group is reduced to the corresponding amine group and is then converted to the isothiocyanate group by reaction with thiophosgene. These compounds are bifunctional chelating agents which can be conjugated to bio-organic molecules for use as diagnostic agents capable of chelating lanthanides. Since attachment of the linker portion of the molecule is through one of the nitrogens of the aminocarboxylic acid, then one potential aminocarboxyl group is lost for chelation. Thus, a DETA-based bifunctional chelant containing four (not five) acid groups is prepared. In this respect this class of bifunctional chelant is similar to those where attachment to the protein is through an amide group with subsequent loss of a carboxyl chelating group.

In the *J. Radioanalytical Chem.* 57(12), 553–564 (1980), Paik et al. disclose the use of p-nitrobenzylbromide in a reaction with a "blocked" diethylenetriamine, i.e. bis-(2-phthalimidoethyl)amine followed by deblocking procedures and carboxymethylation using chloroacetic acid, to give N'-p-nitrobenzyldiethylenetriamine N,N,N'',N''-tetraacetic acid. Again, since the attachment is through a nitrogen, a tetraacetic acid derivative is obtained. Conjugation of the bifunctional chelating agent and chelation with indium is discussed. Substitution on the nitrogen atom is also taught by Eckelman et al. in the *J. Pharm. Sci.* 64(4), (1975) by reacting amines such as "ethylenediamine or diethylenetriamine with the appropriate alkyl bromide before carboxymethylation." The compounds are proposed as potential radiopharmaceutical imaging agents.

Recently Carney, Rogers, and Johnson disclosed (3rd. International Conference on Monoclonal Antibodies; San Diego, Calif.—Feb. 4–6, 1988) abstracts entitled "*Absence of Intrinsically Higher Tissue Uptake from Indium-111 Labeled Antibodies: Co-administration of Indium-111 and Iodine-125 Labeled B72.3 in a Nude Mouse Model*" and "*Influence of Chelator Denticity on the Biodistribution of Indium-111 Labeled B72.3 Immunoconjugates in Nude Mice*". The biodistribution of indium-111 complexed with an EDTA and DTPA bifunctional chelating agent is disclosed. Attachment of the aromatic ring to the EDTA/DTPA moieties is through an acetate radical. Previously Hunt et al. in U.S. Pat. Nos. 4,088,747 and 4,091,088 (1978) disclosed ethylenediaminediacetic acid (EDDA) based chelating agents wherein attachment of an aromatic ring to the EDDA moiety is through the alkylene or acetate radical. The compounds are taught to be useful as chelates for studying hepatobillary function. The preferred metal is technetium-99m. Indium-111 and indium 113 are also taught as useful radionuclides for imaging.

Martell et al. in the *Inorganica Chemica Acta* 138, 215–230 (1987) disclose an iron chelating agent for treating Cooley's anemia. The ligands used were analogs of EDTA with amino and carboxylate donor groups, or having additional donor groups present like phenolic or phenolic groups substituted on pyridine rings; aminophosphonic acid or ester groups with additional phenolate and amino donors; macrocyclic polyamines having carboxylate and/or phenolate donor groups; trishydroxamic acids; triscatechols; and multidentate ligands with coordinating amide groups.

The development of bone metastases is a common and often catastrophic event for a cancer patient. The pain, pathological fractures, frequent neurological deficits and forced immobility caused by these metastatic lesions significantly decrease the quality of life for the cancer patient. The number of patients that contract metastatic disease is large since nearly 50% of all patients who contract breast, lung or prostate carcinoma will eventually develop bone metastases. Bone metastases are also seen in patients with carcinoma of the kidney, thyroid, bladder, cervix and other tumors, and collectively, these represent less than 20% of patients who develop bone metastases. Metastatic bone cancer is rarely life threatening and occasionally patients live for years following the discovery of the bone lesions. Initially, treatment goals center on relieving pain, reducing requirements for narcotic medication and increasing ambulation. Clearly, it is hoped that some of the cancers can be cured.

The use of radionuclides for treatment of cancer metastatic to the bone dates back to the early 1950's. It has been proposed to inject a radioactive particle-emitting nuclide in a suitable form for the treatment of calcific lesions. It is desirable that such nuclides be concentrated in the area of the bone lesion with minimal amounts reaching the soft tissue and normal bone. Radioactive phosphorus (P-32 and P-33) compounds have been proposed, but the nuclear and biolocalization properties limit the utility of these compounds. [Kaplan, E., et al., *J. Nuc. Med.* 1(1), 1, (1960); (U.S. Pat. No. 3,965,254)].

Another attempt to treat bone cancer has been made using phosphorus compounds containing a boron residue. The compounds were injected into the body (intravenously) and accumulated in the skeletal system. The treatment area was then irradiated with neutrons in order to activate the boron and give a therapeutic radiation dose. (U.S. Pat. No. 4,399,817).

In the above mentioned procedures, it is not possible to give therapeutic doses to the tumor without substantial damage to normal tissues. In many cases, especially for metastic bone lesions, the tumor has spread throughout the skeletal system and amputation or irradiation is not practical. (*Seminars in Nuclear Medicine* IX(2), April, 1979).

The use of Re-186 complexed with a diphosphonate has also been proposed. [Mathieu, L. et al., [*Int. J. App. Rad. & Isot.* 30, 725–727 (1979); Weinenger, J., Ketring, A. R., et al., *J. Nuc. Med.* 24(5), 125, (1983)]. However, the preparation and purification needed for this complex limits its utility and wide application.

Strontium-89 has also been proposed for patients with metastic bone lesions. However, the long half-life (50.4 days), high blood levels and low lesion to normal bone ratios can be disadvantageous. [Firusian, N., Mellin, P., Schmidt, C. G., *The Journal of Urology*, 116, 764, (1976); Schmidt, C. G., Firusian, N., *Int. J. Clin. Pharmacol.*, 93, 199–205, (1974)].

A palliative treatment of bone metastases has been reported which employed I-131 labelled α-amino-(3-iodo-4-hydroxybenzylidene)diphosphonate [Eisenhut, M., *J. Nuc. Med.* 25(12), 1356–1361, (1984)]. The use of radioiodine as a therapeutic radionuclide is less than desirable due to the well known tendency of iodine to localize in the thyroid. Eisenhut lists iodide as one of the possible metabolites of this compound. In addition, any I-131 left over from the iodination reaction and not separated in the washing procedure also constitutes a threat to the thyroid.

Aminocarboxylic acids are known to chelate metal ions. Particularly stable chelates are formed with metals from the alkaline earth and transition metal series.

O'Mara et al. (*J. Nuc. Med.* 10, 49–51, 1969) have prepared rare earth complexes of aminocarboxylic acids at chelant to metal ratios of 10:1. They find good skeletal properties and propose their use as diagnostic skeletal agents. In addition to high bone uptake, high amounts of radiation were observed in muscle and/or liver. Of the rare earth nuclides evaluated Sm-153 and Er-171 were indicated as having the most suitable characteristics for imaging in humans. The utility of these agents for therapy, however, is not suggested.

Rosoff, B. et al., *Int. J. App. Rad. and Lot.* 14, 129–135 (1963), disclose complexes of EDTA and NTA with certain radionuclides, namely Sc-46, Y-91, La-140 and Sm-153. The relationship of the stability constant of these complexes to urinary excretion is shown. Chelant to metal molar ratios of 5:1 were employed and high concentrations of radioactivity were observed in the liver, spleen, kidney, lung and bone.

SUMMARY OF THE INVENTION

The present invention is directed to novel chelants possessing ortho ligating functionality, which chelant forms complexes with metals, especially "radioactive" metals having rare earth-type chemistry. Preferred radioactive metals include samarium-153 ($^{153}$Sm), holmium-166 ($^{166}$Ho), yttrium-90 ($^{90}$y), promethium-149 ($^{149}$Pm), gadolinium-159 ($^{159}$Gd), lanthanum-140 ($^{140}$La), lutetium-177 ($^{177}$Lu), ytterbium-175 ($^{175}$Yb), scandium-47 ($^{47}$Sc) and praseodymium-142 ($^{142}$Pr). The complexes so formed can be used by themselves or can be attached to an antibody or fragment thereof and used for therapeutic and/or diagnostic purposes. The complexes and/or conjugates can be formulated for in vivo or in vitro uses. Preferred uses of the formulated conjugates is the treatment of cancer in animals, especially humans.

In addition certain of the chelant-radionuclide complexes can be effectively employed in compositions useful as therapeutic and/or diagnostic agents for calcific tumors and/or in compositions useful as therapeutic agents for the relief of bone pain.

More specifically, the present invention is directed to compounds having the formula: wherein:

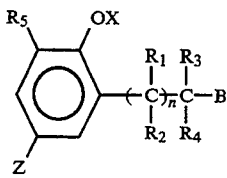

(I)

Z is an electrophilic or nucleophilic moiety which allows for covalent attachment to an antibody or fragment thereof or a synthetic linker which does not interfere with the formation of complexation with a radionuclide and which can be attached to an antibody or fragment thereof;

X is hydrogen, $C_1$–$C_3$ alkyl or $CR_3R_4CO_2H$;

$R_1$, $R_2$, $R_3$ and $R_4$ each are independently hydrogen, hydroxy, $CO_2H$ or a $C_1$–$C_3$ alkyl group;

$R_5$ is hydrogen or $(CR_1R_2)_n CR_3R_4B'$;

B represents a linear or branched polyalkylene polyamine where at least one of the amine hydrogens has been substituted with a $CR_3R_4CO_2H$ group;

B' represents a linear or branched amine or polyalkylene polyamine where at least one of the amine hydrogens has been substituted with a $CR_3R_4CO_2H$ group;

n is 0 or 1; or a pharmaceutically acceptable salt thereof.

Also included within the scope of the present invention are compounds having a chelant posssessing ortho ligating functionality having the formula

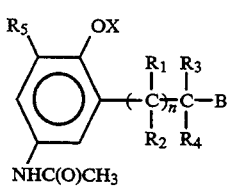

(IA)

wherein:

X is hydrogen, $C_1$–$C_3$ alkyl or $CR_3R_4CO_2H$;

$R_1$, $R_2$, $R_3$ and $R_4$ each are independently hydrogen, hydroxy, $CO_2H$ or a $C_1$–$C_3$ alkyl group;

$R_5$ is hydrogen or $(CR_1R_2)_n CR_3R_4B'$;

B represents a linear or branched polyalkylene polyamine where at least one of the amine hydrogens has been substituted with a $CR_3R_4CO_2H$ group;

B' represents a linear or branched amine or polyalkylene polyamine where at least one of the amine hydrogens has been substituted with a $CR_3R_4CO_2H$ group;

n is 0 or 1; or a pharmaceutically acceptable salt thereof.

It is preferred that the carboxyl group (when present) be attached to the first or second carbon from the nitrogen of the B group, i.e. the carbon α or β to the nitrogen in the chelant moiety. Preferred compounds of formula I are those where n is 0; or $R_1$, $R_2$, $R_3$ and $R_4$ are each hydrogen; or n is 0 and one of $R_3$ or $R_4$ is hydrogen and the other is COOH; or X is hydrogen. When the chelants are to be used as bifunctional chelating agents, then Z is preferably amino, isothiocyanato, semicarbazide, thiosemicarbazide, carboxyl, bromoacetamido or maleimido.

Additionally, the present invention is directed to compounds having the formula:

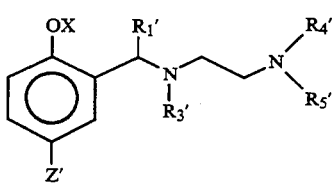

II wherein Z' is hydrogen, $NH_2$, $NO_2$, $NHC(O)CH_3$ or $N(R')_2$, where R' is hydrogen or $C_1$–$C_3$ alkyl;

X is hydrogen, $C_1$–$C_3$ alkyl or $CR_3R_4COOH$;

$R'_1$ is hydrogen or COOH;

$R'_3$, $R'_4$ and $R'_5$ are independently hydrogen or $CR_3R_4COOH$, with the proviso that at least one of $R'_1$, $R'_3$, $R'_4$ and $R'_5$ is hydrogen; or a pharmaceutically acceptable salt thereof.

Furthermore, the present invention is directed to compounds having the formula:

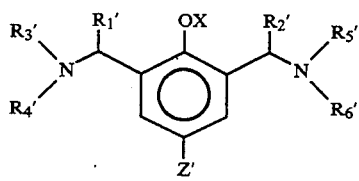

III wherein Z' is selected from the group consisting of hydrogen, $NH_2$, $NO_2$, $NHC(O)CH_3$ or $N(R')_2$, where R' is hydrogen and $C_1$–$C_3$ alkyl;

X is selected from the group consisting of hydrogen, $C_1$–$C_3$ alkyl and $CR_3R_4COOH$;

$R_3$ and $R_4$ are independently selected from the group consisting of hydrogen, $C_1$–$C_3$ alkyl and COOH;

$R'_1$ and $R'_2$ each are independently selected from the group consisting of hydrogen and COOH, with the proviso that at least one is COOH;

$R'_3$, $R'_4$, $R'_5$ and $R'_6$ are independently selected from the group consisting of hydrogen and $CR_3R_4COOH$, with the proviso that at least three are $CR_3R_4COOH$; or a pharmaceutically acceptable salt thereof.

Also included in the scope of this invention are complexes and conjugates and methods of use of the compounds of Formula III. Such complexes comprise the compound complexed with a radionuclide metal ion selected from the group consisting of $^{153}$Sm, $^{166}$Ho, $^{90}$Y, $^{149}$pm, $^{159}$Gd, $^{140}$La, $^{177}$Lu, $^{175}$Yb, $^{47}$Sc and $^{142}$Pr.

The present invention is also directed to radioactive metal ion complexes, especially radioactive rare-earth type metal ion complexes, and to conjugates formed with the aforementioned complexes and antibody or antibody fragments. In addition, the present invention also includes formulations having the chelant-radionuclide complexes and/or the conjugates of the invention and a pharmaceutically acceptable carrier. Typically the pharmaceutically acceptable carrier in these formulations is in liquid form. The invention also includes a method for the diagnosis or treatment of a disease state, especially cancer, in a mammal by the administration to the mammal an effective amount of the formulation.

DETAILED DESCRIPTION OF THE INVENTION

As used herein, the following indicated terms have these meanings: with respect to the definition of Z; "electrophilic" moieties include, but are not limited to, isothiocyanate, bromoacetamide, maleimide, imidoester, thiophthalimide, N-hydroxysuccinimyl ester, pyridyl disulfide and phenyl azide; suitable "nucleophilic" moieties include, but are not limited to, carboxyl, amino, acyl hydrazide, semicarbazide, and thiosemicarbazide; "synthetic linkers" include any synthetic organic or inorganic linkers which are capable of being covalently attached to an antibody or antibody fragment, preferred synthetic linkers are biodegradable synthetic linkers which are stable in the serum of a patient but which have a potential for enzymatic cleavage within an organ of clearance for the radioisotope, for example biodegradable peptides or peptide containing groups. Of the electrophilic moieties isothiocyanate, bromoacetamide and maleimide are preferred, especially preferred is isothiocyanate; and of the nucleophilic moieties amino, carboxyl, semicarbazide and thiosemicarbazide are preferred, especially preferred are amino and carboxyl. It is desirable that the nature and/or position of Z be such that it does not appreciably interfere with the chelation reaction. Z can also be a non-reactive moiety such as H, $NO_2$, $NHC(O)CH_3$, $NR'_2$ (where R' is H or $C_1-C_3$alkyl) when the end use does not involve attachment of the chelate to a protein.

The term "$C_1-C_3$" alkyl includes methyl, ethyl, n-propyl and isopropyl.

The terms "linear or branched amine or polyalkylene amine" mean straight or branched chain alkyl moieties that contain at least one, and usually more than one, nitrogen atom.

As used herein, the term "mammal" means animals that nourish their young with milk secreted by mammary glands, preferably warm blooded mammals, more preferably humans.

"Antibody" refers to any polyclonal, monoclonal, chimeric antibody or heteroantibody, preferably a monoclonal antibody; "antibody fragment" includes Fab fragments and F(ab')$_2$ fragments, and any portion of an antibody having specificity toward a desired epitope or epitopes. When using the term "radioactive metal chelate/antibody conjugate" or "conjugate" the "antibody" is meant to include whole antibodies and/or antibody fragments, including semisynthetic or genetically engineered variants thereof. Preferred antibodies are CC-49 and antibody fragments such as Fab and F(ab')$_2$. Other possible antibodies are CC-83 and B72.3. The hybridoma cell line B72.3 is deposited American Type Culture Collection (ATCC), having the accession number ATCC HB 8108. The other murine monoclonal antibodies bind to epitopes of TAG-72, a tumor associated antigen.

As used herein, "radioactive metal complex" or "complex" refers to a complex of the compound of the invention, e.g. formula I, complexed with a rare-earth type metal ion, especially a radioactive rare-earth type metal ion, where at least one metal atom is chelated or sequestered; "radioactive metal ion chelate/antibody conjugate" or "radioactive metal ion conjugate" refers to a radioactive metal ion conjugate that is covalently attached to an antibody or antibody fragment; "radioactive" when used in conjunction with the word "metal ion" refers to one or more isotopes of the rare-earth type elements that emit particles and/or photons, such as $^{153}$Sm, $^{166}$Ho, $^{90}$Y, $^{149}$pm, $^{159}$Gd, $^{140}$La, $^{177}$Lu, $^{175}$Yb, $^{47}$Sc and $^{142}$Pr. The terms "bifunctional coordinator" "bifunctional chelating agent" and "functionalized chelant" are used interchangeably and refer to compounds that have a chelant moiety capable of chelating a metal ion and a linker/spacer moiety covalently bonded to the chelant moiety that is capable of serving as a means to covalently attach to an antibody or antibody fragment.

As used herein, "pharmaceutically acceptable salt" means any salt of a compound of formula (I) which is sufficiently non-toxic to be useful in therapy or diagnosis of mammals. Thus, the salts are useful in accordance with this invention. Representative of those salts formed by standard reactions from both organic and inorganic sources include, for example, sulfuric, hydrochloric, phosphoric, acetic, succinic, citric, lactic, maleic, fumaric, palmitic, cholic, pamoic, mucic, glutamic, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium, alkali metal ions, alkaline earth metal ions, and other similar ions. Particularly preferred are the salts of the compounds of formula (I) where the salt is potassium, sodium, ammonium, or mixtures thereof.

The bifunctional chelating agents described herein (represented by formula I) can be used to chelate or sequester the rare-earth type metal ions, particularly radioactive rare-earth type metal ions, so as to form metal ion chelates (also referred to herein as "complexes"). The complexes, because of the presence of the functionalizing moiety (represented by "Z" in formula I), can be attached to functionalized supports, such as functionalized polymeric supports, or preferably covalently attached to antibodies or antibody fragments. Thus the complexes described herein may be covalently attached to an antibody or antibody fragment and are referred to herein as "conjugates".

The antibodies or antibody fragments which may be used in the conjugates described herein can be prepared by techniques well known in the art. Highly specific monoclonal antibodies can be produced by hybridization techniques well known in the art, see for example, Kohler and Milstein [*Nature* 256,495–497 (1975); and *Eur. J. Immunol.* 6, 511–519 (1976)]. Such antibodies normally have a highly specific reactivity. In the antibody targeted radioactive metal ion conjugates, antibodies directed against any desired antigen or hapten may be used. Preferably the antibodies which are used in the radioactive metal ion conjugates are monoclonal antibodies, or fragments thereof having high specificity for a desired epitope(s). Antibodies used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. Some examples of antibodies or antibodiy fragraments are CC-11, CC-15, CC-30, CC-46, CC-49 F(ab')$_2$, CC-49, CC-83, CC-83 F(ab')$_2$, CC-92 and B72.3. [See D. Colcher et al., *Cancer*

Res. 48, 4597–4603 (Aug. 15, 1988) for CC-49, CC-83 and B72.3 antibodies.] The following CC antibodies have been deposited in ATCC as follows: CC-11 as HB 9455; CC-15 as HB 9460; CC-30 as HB 9457; CC-46 as HB 9458; CC-49 as HB 9459; CC-83 as HB 9453; and CC-92 as HB 9454. B72.3 has been deposited in ATCC as HB 8108. A more complete list of antigens can be found in U.S. Pat. No. 4,193,983. The radioactive metal ion chelate/antibody conjugates of the present invention are particularly preferred for the diagnosis and treatment of various cancers.

The preferred rare-earth type (lanthanide or pseudo-lanthanide) complexes of the present invention are represented by the formula:

$$C[Ln(BFC)]$$

wherein: Ln is a rare-earth metal (lanthanide) ion, such as $Ce^{3+}+Pr^{3+}+Nd^{3+}+Pm^{3+}+Sm^{3+}+Eu^{3+}+Gd^{3+}+Tb^{3+}+Dy^{3+}+Ho^{3+}+Er^{3+}+Tm^{3+}+Yb^{3+}$ and $Lu^{3+}$, or pseudo-lanthanide metal ion, such as $Sc^{3+}$, $Y^{3+}$ and $La^{3+}$; BFC represents a bifunctional chelant; and C represents a pharmaceutically acceptable ion or group of ions of sufficient charge to render the entire complex neutral. If the BFC contains four or more negatively charged moieties, then C is a cation or group of cations such as $H^+$, $Li^+$, $Na^+$, $K^+$, $Rb^+$, $Cs^+$, $Mg^{2+}$, $Ca^{2+}$, $Sr^{2+}$, $Ba^{2+}$, $Ra^{2+}$, $NH_4^+$, $N(CH_3)^{4+}$, $N(C_2H_5)_4^+$, $N(C_3H_7)_4^+$, $N(C_4H_9)_4^+$, $As(C_6H_5)_4^+$, $[(C_6H_5)_3P=]_2N^+$ and other protonated amines. If the BFC N+ contains three negatively charged moieties, then C is not required. If the BFC contains two negatively charged moieties, then C is an anion such as $F^-$, $Cl^-$, $Br^-$, $I^-$, $ClO_4^-$, $BF_4^-$, $H_2PO_4^-$, $HCO_3^-$, $HCO_2^-$, $CH_3SO_3^-$, $H_3C-C_6H_4-SO_3^-$, $PF_6^-$, $CH_3CO_2^-$ and $B(C_6H_5)_4^-$.

This invention is used with a physiologically acceptable carrier, excipient or vehicle therefor. The methods for preparing such formulations are well known. The formulations may be in the form of a suspension, injectable solution or other suitable formulations. Physiologically acceptable suspending media, with or without adjuvants, may be used.

An "effective amount" of the formulation is used for therapy. The dose will vary depending on the disease being treated. Although in vitro diagnostics can be performed with the formulations of this invention, in vivo diagnostics are also contemplated using formulations of this invention. The conjugates and formulations of this invention can also be used in radioimmuno guided surgery (RIGS); however, other metals which could be used for this purpose also include $^{99m}Tc$, $^{111}In$, $^{113n}In$, $^{67}Ga$ and $^{68}Ga$.

When the chelant-radionuclide complexes of this invention are to be used for the treatment of bone cancer certain criteria must be met. While the properties of the radionuclide are important, the overall properties of the composition containing the radionuclide-chelant complex is the determining factor. The disadvantages of any one property may be overcome by the superiority of one or more of the properties of either ligand or radionuclide and their combination, as employed in the composition must be considered in toto.

The following is a discussion of those criteria which must be considered in choosing any particular combination (i.e., complex) of radionuclide and ligand employed in the compositions of the invention. Radionuclide-chelant complexes, when used in the absence of an appropriate excess of the ligands employed in the invention may not be therapeutically useful or effective.

There is a need, therefore, for compositions possessing the following criteria by which it is possible to deliver therapeutic radiation doses to calcific tumors with minimal doses to soft tissue.

The radionuclide must be delivered preferentially to the bone rather than to soft tissue. Most particularly, uptake in either liver or blood is undesirable.

The radionuclide should be cleared rapidly from non-osseous tissue to avoid unnecessary damage to such tissues, e.g., it should clear rapidly from the blood.

The proposed use for some of the compositions of this invention is the therapeutic treatment of calcific tumors in animals. As used herein, the term "calcific tumors" includes primary tumors, where the skeletal system is the first site of involvement, and metastatic bone cancer where the neoplasm spreads from other primary sites, such as prostate and breast, into the skeletal system. This invention provides a means of alleviating pain and/or reducing the size of, and/or inhibiting the growth and/or spread of, or causing regression of and/or destroying the calcific tumors by delivering a therapeutic radiation dose.

The composition may be administered as a single dose or as multiple doses over a longer period of time. Delivery of the radionuclide to the tumor must be in sufficient amounts to provide the benefits referred to above.

Other uses of some of the chelants of the present invention may include the removal of undesirable metals (i.e. iron) from the body, magnetic resonance imaging, attachment to polymeric supports for various purposes, e.g. as diagnostic agents, and removal of lanthanide metal or pseudo-lanthanide metal ion by selective extraction. In addition the metal-ligand complexes used to deliver radionuclides to calcific sites may have utility for the ablation of bone marrow (i.e. for bone marrow transplants).

Radionuclides can be produced in several ways. In a nuclear reactor a nuclide is bombarded with neutrons to obtain a radionuclide, e.g.

$$Sm\text{-}152 + neutron \rightarrow Sm\text{-}153 + gamma$$

Another method of obtaining radionuclides is to bombard nuclides with particles produced by a linear accelerator or a cyclotron. Yet another way is to isolate the radionuclide from a mixture of fission products. The method of obtaining the nuclides employed in the present invention is not critical thereto.

The chelating agents disclosed herein can be prepared in ways well known to the art. Thus, for example, see Chelating Agents and Metal Chelates, Dwyer & Mellor, Academic Press (1964), Chapter 7. See also methods for making amino acids in *Synthetic Production and Utilization of Amino Acids*, (edited by Kameko, et al.) John Wiley & Sons (1974).

When Z (in the formula) is chosen to be an electrophilic moiety it can be prepared by methods known to the art. Such methods may be found in *Acc. Chem. Res.* 17., 202–209 ( 1984 ).

Examples of some of the methods which may be used to prepare the chelants of formula I, II or III are:

A) reacting a compound of the formula

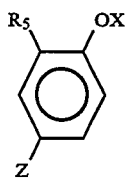

wherein:

Z is an electrophilic or nucleophilic moiety which allows for covalent attachment to an antibody or fragment thereof or a synthetic linker which does not interfere with the formation of complexation with a radionuclide and which can be attached to an antibody or fragment thereof;

X is hydrogen;

$R_5$ is hydrogen or $(CR_1R_2)_nCR_3R_4T$, where $R_1$, $R_2$, $R_3$ and $R_4$ each are independently hydrogen, hydroxy, $CO_2H$ or a $C_1$-$C_3$ alkyl group, n is 0 or 1, and T represents a linear or branched amine or polyalkylene amine where at least one of the amine hydrogens has been substituted with a $CR_3R_4CO_2H$ group; or a pharmaceutically acceptable salt thereof; with a compound B and an aldehyde or aldehyde precurser equivalent, where B represents a linear or branched amine or polyalkylene amine where there is at least one amine hydrogen;

in the presence of caustic and a suitable solvent, at a temperature of 20° C. or less, followed by heating and separating the desired product of formula I, II or III;

B) reacting the product obtained from Step (A) with a halo-$(CR_1R_2)_nCR_3R_4$ acid, at a pH of 9 or higher, in the presence of caustic, at a temperature of 20° C. or less, to provide the compounds of formula I, II or III where at least one of $R_1$, $R_2$, $R_3$ and $R_4$ is $CO_2H$;

C) hydrolyzing the product of Step (B) where Z is $NHC(O)CH_3$ with NaOH in $H_2O$, to provide the products of formula I, II or III where Z is $NH_2$;

D) reacting the product obtained from Step (A) with glyeolonitrile, in caustic, at a pH of 9 or higher, at a temperature of 20° C or less, followed by hydrolysis of the cyano group with HCl in $H_2O$, to provide the products of formula I, II or III where at least one of $R_1$, $R_2$, $R_3$ and $R_4$ is $CO_2H$;

E) hydrolyzing the product of Step (A) where Z is $NHC(O)CH_3$ with DCl in $D_2O$, with heating, to provide the products of formula I, II or III where Z is $NH_2$; and F) reacting the product obtained from any one of Steps (A) through (E), where Z is $NH_2$, with thiophosgene to provide the products of formula I, II or III where Z is isothiocyanato.

The reaction conditions and reagents for the various steps above are as follows. When the temperature is "20° C. or less" this is usually accomplished by use of an ice/water bath. "Heating" is done either at reflux or above room temperature. The preferred "caustic" is sodium hydroxide, but any suitable base the is able to maintain the desired pH without adverse effect on the product formed from the reaction is acceptable. A "suitable solvent" is inert and provides solubility for the reactants, examples of such solvents are water, and alcohols such as methanol. The desired product may be seperated by any conventional methods, for example precipitation from a solvent such as acetone.

The complexes of formula I, II or III are prepared by conventional methods, for example by reacting the chelant with the metal under conditions such that the metal is sequestered by the chelant. Frequently, the chelant is in excess to that of the metal.

The conjugates of formula I, II or III are prepared by conventional methods, for example by covalently attaching the complex to an antibody or antibody fragment.

The invention will be further clarified by a consideration of the following examples, which are intended to be purely exemplary of the use of the invention. Structures of compounds with reference to the generic formula I are shown in Table I.

Preparation of Starting Materials

EXAMPLE A. PREPARATION OF UNSYMMETRICAL ETHYLENE-DIAMINEDIACETIC ACID.

Deionized water (60.6 g), 98% N-acetylethylenediamine (20.4 g, 0.2 mole), and bromoacetic acid (55.7 g, 0.40 mole) were added to a reaction vessel and cooled in an ice-water bath. The pH of the mix was adjusted, while stirring, to approximately 8.1 with 25% sodium hydroxide solution. The temperature of the mix was maintained at less than 20° C. during the caustic addition. The ice-water bath was removed and the pH maintained between 7 and 8 by the addition of 25% sodium hydroxide solution. The temperature was controlled at less than 37° C. by periodically cooling with an ice-water bath. The reaction mixture was stirred and maintained as above for approximately 31 hours and then transferred to a round-bottom reaction flask equipped with a water-cooled reflux condenser, magnetic stirrer bar, thermometer, addition funnel and a heating mantle. Sodium hydroxide solution (40.1 g of 50% solution) was added and the mix heated, with stirring, at reflux for approximately 15 hours and then cooled and filtered using a medium glass frit funnel and vacuum. The filtrate was transferred quantitatively (using deionized water) to a beaker and cooled in an ice-bath to less than 25° C. Deionized water (100 ml) was added with stirring and the pH adjusted to approximately 4 with concentrated hydrochloric acid while maintaining the temperature at less than 25° C. The mix was filtered using a medium glass frit funnel and vacuum. Approximately 1200 ml of ethanol were added to a large beaker and stirred with a magnetic stirrer bar. The filtrate from above was added to the ethanol with thorough mixing. An oily material forms which gradually turns into a white solid. Agitation was continued for two hours at which time the solids were collected by filtering using a medium glass frit funnel and vacuum. The solids were allowed to dry by exposure to air for about 1.5 hours and then placed in a vacuum oven and dried at 55°–60° C. for several hours. Approximately 42.9 g of white solids containing inorganic salt were collected and identified as unsymmetrical ethylenediaminediacetic acid by proton and carbon NMR.

EXAMPLE B. PREPARATION OF 2-OXO-1-PIPERAZINEACETIC ACID; LACTAM OF ETHYLENEDIAMINEDIACETIC ACID.

Deionized water (150 g), 25.0 g (0.14 mole) of symmetrical ethylenediaminediacetic acid, and 28 g of concentrated hydrochloric acid were added to a round-bottom reaction flask equipped with a thermometer, temperature controller, water-cooled reflux condenser, and heating mantle. The mixture was stirred with a magnetic stirrer bar and heated at reflux for four hours and cooled. The contents were filtered using a medium glass frit funnel and vacuum. The pH of the filtrate was adjusted to approximately 1.5 with 50% sodium hydroxide solution and filtered with a medium glass frit funnel using vacuum. The pH of the filtrate was adjusted to about 5 with 50% sodium hydroxide solution and the volatiles removed (in vacuo) at a temperature of 60°–70° C. The solids were dried in a vacuum oven at 55°–60° C. for several hours. The lactam of symmetrical ethylenediaminediacetic acid was confirmed by proton and carbon NMR.

EXAMPLE C. PREPARATION OF 2-OXO-1,4-PIPERAZINEDIACETIC ACID; LACTAM OF ETHYLENEDIAMINETRIACETIC ACID.

Approximately 40.8 g of 2-oxo-1-piperazineacetic acid, prepared by the procedure of Example B, and 70 g of deionized water were added to a beaker and stirred for several hours with a magnetic stirrer bar. The contents were filtered using a medium glass frit funnel and vacuum. The filtrate and 20.0 g of bromoacetic acid were added to a beaker and stirred till all the bromoacetic acid had dissolved. The pH was adjusted to approximately 7 with 25% sodium hydroxide solution. The temperature was maintained at less than 25° C. during the caustic addition by cooling in an ice-water bath. The ice-water bath was removed and the mix allowed to stir for approximately 4–5 hours at approximately 35° C. while maintaining the pH at about 7 by the periodic addition of 25% sodium hydroxide solution. The reaction mix was allowed to stand for several hours and then concentrated (in vacuo) to a weight of approximately 90–100 g and filtered using a medium glass frit funnel and vacuum. Volatiles were removed (in vacuo) from the filtrate at a temperature of 55°–60° C. and the material dried in a vacuum oven at 55°–60° C. for several hours. The lactam of ethylenediaminetriacetic acid was confirmed by proton and carbon NMR.

EXAMPLE D. PREPARATION OF TRISODIUM ETHYLENEDIAMINETRIACETIC ACID.

Approximately 44.5 g of the crude 2-oxo-1,4-piperazinediacetic acid, prepared by the procedure of Example C, and 280 g of deionized water were added to a beaker and agitated till the lactam had dissolved. Caustic solution (110 g, 50%) was added with agitation. The temperature was maintained at less than 25° C. by cooling in an ice-bath. Hydrolysis was then achieved by immersing tubes containing the solution into a water bath controlled at 87° C. After 15 minutes, the solutions were removed and cooled in an ice-water bath. Analysis by proton and carbon NMR confirmed the presence of trisodium ethylenediaminetriacetic acid in the alkaline hydrolysis medium.

EXAMPLE E. PREPARATION OF 4-DIETHYLENETRIAMINEACETIC ACID.

To a flask equipped with a water-cooled reflux condenser, magnetic stirrer and thermometer were added 75.0 g of phthalic anhydride, 350.5 g of acetic acid and 26.0 g of diethylenetriamine. The mix was stirred and heated at approximately 116° C. for 1.5 hours and then cooled. Volatiles were removed under vacuum at 65°–70° C. until a weight of 218 g was obtained. The mixture was poured into 600 g of ethanol with stirring. After two hours the solids were filtered using a medium glass frit funnel. The solids were washed twice with 500 ml of ethanol and then dried in a vacuum oven at 60°–65° C. Approximately 66 g of material of the diphthaloyl compound were collected.

The ethyl ester of the diphthaloyl compound was prepared by adding 65.6 g of the above prepared diphthaloyl compound, 17.7 g of sodium carbonate and 800 ml of ethanol to a flask equipped with a water-cooled reflux condenser, addition funnel, mechanical stirrer and a thermometer with a temperature controller. Ethyl bromoacetate (51.0 g) was added over a 15 minute period to the stirred mixture and then heated at reflux for 16 hours. Ethanol was removed (200 ml) by distillation using a Dean-Stark distillation trap and the remaining reaction mixture cooled to less than 5° C. by the addition of crushed ice. The mixture was cooled for an additional 5 hours in an ice bath and filtered using a medium glass frit funnel. The solids were washed twice with ethanol and dried in a vacuum oven at 65°–70° C. Approximately 81 g of ethyl 1,7-diphthaloyl-4-diethylenetriamineacetate were obtained. In 0.32 g of water and 76.4 g of concentrated hydrochloric acid was dissolved 20.1 g (0.045 moles) of ethyl 1,7-diphthaloyl-4-diethylenetriamineacetate with heating to 93° C. and the mixture held at 93° C. for 6.5 hours. The resulting white precipitate was filtered and washed with water. The combined filtrate was concentrated at 60° C. under vacuum to give a white solid. NMR analysis indicated that the phthaloyl groups were not completely hydrolyzed. The two solids were then combined and added to concentrated hydrochloric acid with a small amount of water. The slurry was then heated to reflux for 6 hours, cooled to room temperature and filtered to give 12.3 g of phthalic acid. The filtrate was then evaporated under vacuum to give 13.9 g of product as a yellow solid. The product was dissolved in water by the addition of 6 g of 50% sodium hydroxide and treated with activated charcoal at 100° C. followed by filtration and evaporation under vacuum to give 15.2 g 4-diethylenetriamineacetic acid.

Preparation of Final Products

EXAMPLE 1. PREPARATION OF 2-[(2-{[BIS(CARBOXYMETHYL)]AMINO}ETHYL ) AMINO]-2-( 5-ACETAMIDO-2-HYDROXYPHENYL )-ETHANOI C ACID.

Deionized water (10.3 g), 98% 4-acetamidophenol (15.1 g 0.1 mole), 50% aqueous glyoxylic acid (14.8 g, 0.1 mole), and methanol (50.5 g) were added to a beaker and mixed using a magnetic stirrer bar. Unsymmetrical ethylenediaminediacetic acid (19.5 g), prepared by the procedure of Example A, was added and the mix cooled in an ice-water bath. The pH of the mix was adjusted, while stirring, to approximately 8.0 with 50% sodium hydroxide solution. The temperature of the mix was maintained at less than 20° C. during the caustic addition. The ice-water bath was removed and the mix adjusted to pH 8.7 and stirred at 25°–32° C. for approximately 2 hours. The mix was transferred to a round-bottom reaction flask equipped with a water-cooled reflux condenser, magnetic stirrer bar, thermometer, and a heating mantle. The mix was heated, with stirring, at 70° C. for 8 hours and then cooled and filtered using a medium glass frit funnel and vacuum. The solids were allowed to dry by exposure to air for 7 hours and then placed in a vacuum oven and dried at 55°–60° C. for several hours. Approximately 29.6 g of solids were collected. The material was then agitated with approximately 300 g of acetone and filtered using a medium glass frit funnel and house vacuum. The solids were washed once again with an additional 300 g of acetone, air dried and then placed in a vacuum oven for one hour at 55°–60° C. Approximately 26.7 g of 2-[(2-{[bis(carboxymethyl)]-amino}ethyl)amino]-2-(5-acetamido-2-hydroxyphenyl)ethanoic acid, sodium salt were collected. These solids and 180 g of deionized water were placed in a beaker and stirred with a magnetic stirrer bar. The pH was adjusted to 2.2 with concentrated hydrochloric acid at which point the acid form of the product began to precipitate from solution. The product was collected by filtration and washed with approximately 150 g of deionized water. The product, 2-[(2-{[bis(carboxymethyl)]amino}ethyl)amino]-2-(5-acetamido-2-hydroxyphenyl)ethanoic acid was dried in a vacuum oven at 55°–60° C. for several hours. Approximately 14.2 g of product were obtained. Proton NMR verified the structure of the product. (See Table I.)

EXAMPLE 2. PREPARATION OF 2-[(2-{[BIS(CARBOXYMETHYL)]-AMINO}ETHYL)(CARBOXYMETHYL)AMINO]-2-[5-ACETAMIDO-2-(CARBOXYMETHYLOXY)-PHENYL]ETHANOIC ACID.

Deionized water (4.5 g), bromoacetic acid (2.0 g) and 2-[( 2-{[bis(carboxymethyl)]amino}ethyl)amino]-2-(5-acetamido-2-hydroxyphenyl) ethanoic acid (2.5 g), prepared by the procedure of Example 1, were added to a small reaction vessel and cooled in an ice-water bath. The pH of the mix was adjusted, while stirring, to approximately 9.3 with 25% sodium hydroxide solution. The temperature of the mix was maintained at less than 20° C. during the caustic addition. The ice-water bath was removed and the mix allowed to stir for 48 hours at a temperature of 35°–40° C. while maintaining the pH between 10.5 and 11.5 by the periodic addition of 25% sodium hydroxide solution. A portion of the reaction mixture (10.2 g) was added to a beaker and stirred with a magnetic stirrer bar. Acetone (125 g) was added to the solution over a 15-minute period resulting in the precipitation of an oil. The acetone portion was removed by decanting and an additional 50 g of acetone added to the precipitate, mixed, and the acetone layer removed. The oil was air dried and then dried in a vacuum oven at 60°–65° C. for about two hours to give a crispy yellow solid. The product was purified by anion exchange chromatography on Q-Sepharose ™ from Pharmacia Inc. on a 15 mm ×500 mm column eluting with a gradient of 0–30% formic acid over two hours at a rate of 3 ml/min and collecting fractions. The fractions were monitored by UV absorption and the appropriate fractions combined and lyophilized to give the desired product. (See Table I.)

EXAMPLE 3. PREPARATION OF 2-[( 2-{[BIS(CARBOXYMETHYL)]AMINO}ETHYL)(CARBOXYMETHYL)AMINO]-2-[5-AMINO-2-(CARBOXYMETHYLOXY)PHENYL]ETHANOIC ACID, PENTA SODIUM SALT.

Approximately 40 mg of 2-[(2-{[bis(carboxymethyl)]amino}ethyl) (carboxymethyl)amino]-2-[5-acetamido-2-(carboxymethyloxy)phenyl]ethanoic acid, prepared by the procedure of Example 2, was dissolved in 700 μl of D₂O and adjusted with NaOD/D₂0 to pH 13. Hydrolysis of the N-acetyl group to the corresponding aniline functionality proceeded at ambient temperature and was followed by proton NMR which confirmed the structure. (See Table I.)

EXAMPLE 4. PREPARATION OF 2-[(2-{[BIS(CARBOXYMETHYL)]AMINO}ETHYL)(CYANOMETHYL)AMINO]-2-(5-ACETAMIDO-2-HYDROXYPHENYL)ETHANOIC ACID.

Deionized water (3.1 g) and 2.5 g of 2-8 (2{[bis(carboxymethyl)]amino}ethyl) amino]-2-(5-acetamido-2-hydroxyphenyl)ethanoic acid, prepared by the procedure of Example 1, were added to a small glass vessel and cooled in an ice-water bath. The pH was adjusted to 9.8–9.9 with 25% sodium hydroxide solution. The temperature of the mix was maintained at less than 20° C. during the caustic addition. The ice-bath was removed and 1.0 g of an aqueous 40% glycolonitrile solution was added with mixing and the pH adjusted to 9.9–10.0 with 25% sodium hydroxide solution. The mix was transferred to a small reaction flask equipped with a thermometer containing a temperature controller, water cooled reflux condenser, and heating mantle. The reaction mixture was stirred with a magnetic stirrer bar and heated at 49°–50° C. for eight hours, cooled and allowed to stand at ambient temperature for 72 hours. A portion of the reaction mixture (8.5 g) was added to a beaker and stirred with a magnetic stirrer bar. Acetone (146 g) was added to the solution over a 10-minute period, resultng in the precipitation of a solid material. The acetone portion was removed by decanting and an additional 50 g of acetone added to the precipitate, mixed, and the acetone layer removed. The material was dried in a vacuum oven at 60°–65° C. for about four hours. Approximately 2.9 g of product was collected. Proton NMR supported the desired aminoacetonitrile derivative. (See Table I.)

EXAMPLE 5. PREPARATION OF 2-[(2-{[BIS(CARBOXYMETHYL)]-AMINO}ETHYL)(CARBOXYMETHYL)AMINO]-2-(5-AMINO-2HYDROXYPHENYL)ETHANOIC ACID.

Approximately 1.0 g of 2-[(2-{[bis(carboxymethyl)]amino}ethyl) (cyanomethyl)amino]-2-(5-acetamido-2-hydroxyphenyl)ethanoic acid, prepared above by the procedure of Example 4, was hydrolyzed under acidic conditions to convert the aminoacetonitrile functionality to the corresponding acetate group and the N-acetyl group to the aniline group. The aminoacetonitrile compound, 2.2 g of D₂O, and 7.8 g of 20% DCl were added to a glass tube. The tube was placed in a temperature-controlled water bath at 88°–89° C. for a total of 33 minutes and then removed and cooled. The hydrolysis was followed by proton NMR. The solution was then freeze-dried and lyophilized to give 1.3 g of solids. The product was purified by anion exchange (Q-Sepharose ™) on a 15 mm ×500 mm column eluting with a gradient of 0–1M acetic acid over one hour at a rate of 3 ml/min and collecting 6 ml fractions. The fractions were monitored by UV absorption and the appropriate fractions were combined and lyophilized to give the desired product. (See Table I.)

EXAMPLE 6. PREPARATION OF 2-[BIS(2-{[(BIS(CARBOXYMETHYL)-]AMINO}ETHYL)AMINO]-2-[5-ACETAMIDO-2-(CARBOXYMETHYLOXY)PHENYL]ETHANOIC ACID AND 2-[{2-[(2-{[BIS(CARBOXYMETHYL)-]AMINO}ETHYL)(CARBOXYMETHYL)AMINO]ETHYL}(CARBOXYMETHYL)AMINO]-2-[5-ACETAMIDO-2-(CARBOXYMETHYLOXY)-PHENYL]ETHANOIC ACID.

Deionized water (24.8 g), 15.1 g (0.1 mole) of 98% 4-acetamidophenol, and 14.8 g of 50% aqueous glyoxylic acid (0.1 mole) were added to a beaker and cooled in an ice-water bath. The pH of the mix was adjusted to 3.3 with 25% sodium hydroxide solution while maintianing the temperature at less than 20° C. DETA (9.8 g) was then added. Once again the temperature was kept below 20° C. by cooing in an ice-water bath. The pH after addition of the DETA was approximately 10.2. The mix was transferred to a reaction flask equipped with a thermometer, a temperature controller, water-cooled reflux condenser, and heating mantle. The reaction mixture was stirred with a magnetic stirrer bar and heated at 75° C. for approximately seven hours and cooled. Acetone (1400 g) was added to a large beaker and stirred with a magnetic stirrer bar. Approximately 40 g of the reaction solution prepared above was added over a 10 minute period resulting in the precipitation of a solid material. The acetone portion was removed by decanting and an additional 1460 g of acetone added and the solid titurated and mixed thoroughly under acetone. The solids were recovered by filtering using a medium glass frit funnel and vacuum. The solids were washed with a copious amount of acetone and then dried in a vacuum oven at a temperature of 60°–65° C. for several hours. Approximately 7.8 g of solids were recovered with proton NMR showng a mixture of the desired isomers of the DETA compound.

Deionized water (5.3 g) and 4 g of the above isolated solids were added to a beaker and stirred with a magnetic stirrer bar for about three hours at which time the solids had completely dissolved. Bromoacetic acid (10.1 g) was added with stirring and the mix cooled in an ice-water bath. The pH of the mix was adjusted to approximately 11 with 25% sodium hydroxide solution. The temperature was maintained at less than 20° C. during the caustic addition. The ice-water bath was removed and the mix allowed to stir for 50 hours at a temperature of 35°–40° C. while maintaining the pH between approximately 10.5–11.5 by the periodic addition of 25% sodium hydroxide solution. Acetone (240 g) was added to a beaker and stirred with a magnetic stirrer bar. Approximately 5 g of the reaction solution was added to the acetone resulting in the precipitation of a solid. The acetone portion was decanted and an additional 245 g of acetone added, mixed and the acetone layer removed. The solids were collected by filtering using a medium glass frit funnel and vacuum. The solids were washed with acetone and then dried in a vacuum oven at 55°–60° C. for several hours. Approximately 2.6 g of solids were collected. (See Table I.)

EXAMPLE 7. PREPARATION OF 2-[BIS(2-{[(BIS(CARBOXYMETHYL)-]AMINO}ETHYL)AMINO]-2-[5-AMINO-2-(CARBOXYMETHYLOXY)PHENYL]ETHANOIC ACID AND 2-[{2-[(2-{[BIS(CARBOXYMETHYL)]AMINO}ETHYL)(CARBOXYMETHYL)AMINO]ETHYL}(CARBOXYMETHYL)AMINO]-2-[5-AMINO-2-(CARBOXYMETHYLOXY)PHENYL]ETHANOIC ACID.

Approximately 376 mg of 2-[bis(2-{[(bis(carboxymethyl)]amino}ethyl) amino]-2-[5-acetamido-2-(carboxymethyloxy)phenyl]ethanoic acid and 2-[{2-[(2-{[bis(-carboxymethyl)]amino}ethyl)(carboxymethyl)amino]ethyl} (carboxymethyl)amino]-2-[5-acetamido-2-(carboxymethyloxy)phenyl]ethanoic acid, prepared by the procedure of Example 6, was dissolved in 1.0 g of D20 and treated with 5 drops of 37% DC1. The acidic solution was then heated at 80° C. for 2 hours after which time the proton NMR spectrum indicated that virtually all of the acetanilide groups had been converted to aniline groups and acetic acid. The solution was then frozen in a dry-ice acetone bath and lyophilized overnight to yield the desired product as a light brown solid. (See Table I.)

EXAMPLE 8. PREPARATION OF 2-[{2-[(2-{[BIS(CARBOXYMETHYL)]-AMINO}ETHYL) (CARBOXYMETHYL) AMINO]ETHYL}(CARBOXYMETHYL)AMINO]-2-[5-AMINO-2-CARBOXYMETHYLOXY)PHENYL]ETHANOIC ACID.

In 40 ml of water was dissolved 8.0 g of 4-diethylenetriamineacetic acid, prepared by the procedure of Example E, and then the mixture was cooled in an ice bath. To this cooled solution was added 6.08 g (0.04 moles) of 4-acetamidophenol and a chilled solution of 5.95 g (0.04 moles) of a 50 weight % solution of glyoxylic acid in water. While keeping the slurry at less than 20° C. with the ice bath, a 2.5 ml portion of 50 weight % sodium hydroxide was added. The resulting slurry at pH 8.75 was heated slowly to 80° C., held at this temperature for 4.5 hours with stirring, then allowed to cool overnight. The solution was then evaporated under vacuum to about 25 ml volume and added to 300 ml of acetone. The acetone was decanted from the resulting solid. The solid was washed several times with acetone and dried to give 26.1 g of product as a dark sticky solid. A 26.05 g portion of this solid was dissolved in 50 ml of water. Into this solution was dissolved 26.7 g (0.192 moles) of bromoacetic acid. The resulting solution was cooled in an ice bath, the pH adjusted to 10.5 with 50 weight % sodium hydroxide, allowed to warm to room temperature, and then heated to 46° C. The temperature was kept at 46° C. and the pH kept at 10.5 by addition of 50 weight % sodium hydroxide for about 23 hours. The volume was then reduced to 50 ml under vacuum. The concentrated solution was added to 500 ml of acetone with vigerous stirring and the resulting precipitate allowed to settle. The acetone was decanted and an additional 400 ml of acetone was added, vigerously stirred and then decanted. A final wash in the same manner using 100 ml of acetone was done. The solid was dried under vacuum to give 52.55 g of crispy brown solid. A 2.00 g sample of this brown solid was dissolved in 20 ml of water and treated with 1.48 g of concentrated hydrochloric acid. This solution was heated at 80° C. until analysis by proton NMR indicated complete hydrolysis of the N-acetyl moiety. The solution was then freeze dried to give 2.13 g of brown solid containing the title product. (See Table I.)

EXAMPLE 9. PREPARATION OF 2-[(2-[(2-[(2-{[BIS(CARBOXYMETHYL)-]AMINO}ETHYL) (CARBOXYMETHYL)AMINO]ETHYL) (CARBOXYMETHYL)AMINO]ETHYL)(CARBOXYMETHYL)AMINO]-2-[5-ACETAMIDO2-(CARBOXYMETHYLOXY) PHENYL]ETHANOIC ACID AND 2[(2-[(2-{[BIS(CARBOXYMETHYL)]AMINO}ETHYL)(CARBOXYMETHYL) AMINO]ETHYL)(2-{[BIS(CARBOXYMETHYL)-]AMINO}ETHYL)AMINO]-2-[5-ACETAMIDO-2-(CARBOXYMETHYLOXY) PHENYL]ETHANOIC ACID.

Deionized water (12.5 g), 98% 4-acetamidophenol (7.6 g), and 50% aqueous glyoxylic acid solution (7.4 g) were added to a beaker and cooled in an ice-water bath. The pH of the mix was adjusted to 3.6 with 25% sodium hydroxide solution while maintaining the temperature at less than 20° C. Linear triethylenetetraamine (7.2 g) was added while keeping the temperature below 20° C. The pH after addition of the triethylenetetraamine was approximately 10.6. The mix was transferred to a reaction flask equipped with a thermometer containing a temperature controller, water cooled reflux condenser, and heating mantle. The reaction mixture was stirred with a magnetic stirrer bar and heated at 80°-83° C. for 4.5 hours and cooled. Acetone (175 g) was added to a beaker and stirred with a magnetic stirrer bar. Approximately 12 g of the reaction solution was added resulting in the precipitation of an oil. The acetone portion was removed by decanting and an additional 175 g of acetone addded and stirring continued. The acetone portion was removed and the precipitant dried in a vacuum oven at 60°-65° C. for several hours. Approximately 3.1 g of solids were collected. The solids were then slurried in 100 g of acetone, thoroughly mixed and filtered using a medium glass frit funnel and vacuum. The solids were then washed with an additional 250 ml of acetone and dried once again in a vacuum oven at 60°-65° C. for about four hours. Approximately 2.0 g of material was recovered with proton NMR indicating a mixture of the triethylenetetraamine isomers present.

Deionized water (2.0 g) and 1.86 g of the above solid product were added to a beaker and stirred for one hour at which time the solids were mostly dissolved. Bromoacetic acid (5.0 g) was added with stirring and the mix cooled in an ice-water bath. The pH of the mix was adjusted to approximately 10.5 and maintained for 47 hours at a temperature of 35°-40° C. while maintaining the pH between 10.5-11.5 by the periodic addition of 25% sodium hydroxide solution. Acetone (130 g) was added to a beaker and stirred with a magnetic stirrer bar. Approximately 10.8 g of the reaction solution was added to the acetone resulting in the precipitation of a solid. The acetone portion was decanted and an additional 150 g of acetone added to the precipitate, mixed, and the acetone layer removed. The solids were dried in a vacuum oven at 60°-65° C. for several hours. Approximately 7.2 g of solids were collected. (See Table I.)

EXAMPLE 10. PREPARATION OF 2,6-BIS{[BIS(CARBOXYMETHYL)AMINO](CARBOXY)METHYL}-4-(ACETAMIDO) PHENOL

To a beaker was added 38.6 g of 98% 4-acetamidophenol, 35.3 g of 98% iminodiacetic acid, 150 mls. of methanol, 38.5 g of 50% aqueous glyoxylic acid solution, and 30 g of deionized water. The mix was cooled in an ice-water bath and the pH adjusted while mixing to approximately 9.4 with 50% sodium hydroxide solution. The temperature was maintained at less than 30° C. during the caustic addition. The mix was transferred to a reaction flask equipped with a water cooled reflux condenser, thermometer, and heating mantle. The reaction mixture was heated to approximately 74°-76° C. and the pH monitored and kept between 8.7-9.5 by the periodic addition of 50% sodium hydroxide solution. The mix was heated for a total of 18 hours. During this time approximately 40 g of deionized water were added. After cooling, the reaction mix was filtered using a medium glass frit and vacuum. Deionized water (75 g) was added to the filtrate and the methanol removed in vacuo at ambient temperature (about 20°-25° C.). The solution was allowed to stand for several hours and the precipitated solids removed from solution by filtering using a medium glass frit funnel and vacuum. Approximately 30 g of the filtrate and 15 g of ethyl ether were mixed thoroughly and the ether layer then separated. The process was repeated using 15 g and 10 g of ethyl ether in succession. The aqueous layer was adjusted with aqueous hydrochloric acid solution to a pH of about 0.5 and volatiles removed in vacuo at a temperature of 50°-55° C. Approximately 13.5 g of solids were collected. Methanol (75 g) was added to the solids and the insoluble salts removed by filtration. Methanol was removed (in vacuo) and the remaining solids dried in a vacuum oven at 70°-75° C. for several hours. The product, which still contained some inorganic salt, was analyzed by proton NMR and found to be predominately the bis-substituted product. (See Table I.)

EXAMPLE 11. PREPARATION OF 2,6-BIS{[(2{[BIS(CARBOXYMETHYL)-]AMINO}ETHYL) (CARBOXYMETHYL)]AMINOMETHYL}-4-(ACETAMIDO) PHENOL.

The alkaline trisodium ethylenediaminetriacetic acid solution, prepared by the procedure of Example D, was cooled in an ice-bath and hydrochloric acid added with stirring to obtain a pH of about 13.8. The temperature was maintained at less than 35° C. during the acid addition. Volatiles were removed (in vacuo) at ambient temperature to a weight of 210 g. The solids were removed by filtering on a medium glass frit funnel using vacuum. The filtrate was transferred to a 250 ml round-bottom flask equipped with a water-cooled reflux condenser, magnetic stirrer bar, thermometer, temperature controller, heating mantle, and addition funnel. The pH was adjusted to about 11 with hydrochloric acid. The temperature was maintained at less than 30° C. during the acid addition. The mix was heated to approximately 40° C. and 11.6 g of 37% aqueous formaldehyde solution added dropwise from the addition funnel over a 35 minute period. The reaction mixture was stirred and heated for an additional 30 minutes and then cooled. The solution was adjusted with 25% sodium hydroxide solution to a pH of about 9.8 and transferred to an addition funnel. To a beaker was added 10.3 g of 98%

4acetamidophenol, 25.2 g of deionized water, and 9.5 g of 25% sodium hydroxide solution. The mix was stirred till complete dissolution was obtained. The solution was transferred to a round-bottom reaction flask equipped as described above and heating and stirring initiated. The mix was heated to approximately 65° C. at which point the formaldehyde adduct solution prepared above was added dropwise over approximately a one hour period. The reaction was stirred and heated at 65° C. for an additional 12 hours and then cooled. Acetone (150 g) was added to a beaker and stirred with a magnetic stirrer bar. Approximately 10 g of the crude reaction mixture was added to the acetone resulting in the precipitation of an oily material. The acetone portion was decanted and an additional 150 g of acetone added to the precipitate, mixed, and the acetone layer removed. The material was dried in a vacuum oven at 55°–60° C. for several hours. Approximately 3.1 g of solids were collected. Approximately 165 mg of the solids were dissolved in a minimum of water and loaded onto a Q-Sepharose TM (from Pharmacia Inc.) column [1.5 cm × 50 cm., acetate form]and eluted using a gradient of 0 to 1M ammonium acetate over two hours at 2 ml/min. The absorbance at 300 nm was observed. The product was contained in the third major peak. This was isolated and freeze-dried to yield 36.4 mg of solids which was characterized by proton and carbon NMR and fast atom bombardment mass spectrometry as 2,6bis{[(2-{[bis(carboxymethyl)]amino}ethyl)(carboxymethyl)]aminomethyl}-4-(acetamido)phenol. (See Table I.)

EXAMPLE 12. PREPARATION OF 2,6-BIS{[(2{IBIS(CARBOXYMETHYL)]AMINO}ETHYL) (CARBOXYMETHYL)]AMINOMETHYL}-4-(AMINO) PHENOL.

Approximately 264 mg. of 2,6-bis{[(2-{[bis(carboxymethyl)]amino}ethyl)(carboxymethyl)]aminomethyl}-4(acetamido)phenol, prepared by the procedure of Example 11, was placed in a 5 mm NMR tube and dissolved in a mixture of D2O (0.5 ml) and DCL (0.5 ml, 20%). The NMR tube was placed in a hot water bath (85° C.) for short periods of time and the reaction progress monitored by NMR (disappearance of the acetamide methyl protons and appearance of acetic acid). After 35 minutes the reaction was complete. The reaction mixture was freeze-dried to yield the crude amine hydrochloride as a dark solid material. The crude product was dissolved in a minimum amount of water and loaded onto a Q-Sepharose$^{TM}$ column (1.5 cm × 50 cm, acetate form) and eluted using a gradient of 0 to 1M ammonium acetate over three hours at 2 ml/min. The absorbance at 300 nm was observed. The product was contained in the third major peak. This was isolated and freeze-dried to leave a pale amber solid (122 mg) which was a mixture of the desired amine product and ammonium chloride. The product mixture was characterized by proton and carbon NMR and elemental analysis. The salt-containing product (250 mg from combined batches) was further purified on Q-Sepharose$^{TM}$(1.5 cm × 50 cm, formate form) using a gradient of 0 to 10% formic acid over four hours. The absorbance at 300 nm was observed. The first major peak contained the desired product. This was isolated and freeze-dried to yield 8.3 mg of a white crystalline solid. The structure was confirmed by proton and carbon NMR and fast atom bombardment mass spectrometry. (See Table I.)

EXAMPLE 13. PREPARATION OF 2,6-BIS{[(2-{[BIS(CARBOXYMETHYL)]AMINO}ETHYL) (CARBOXYMETHYL)]AMINOMETHYL}-4-(ISOTHIOCYANATO)-PHENOL.

Product containing 2,6-bis{[(2-{[bis(carboxymethyl)]amino}ethyl) (carboxymethyl)]aminomethyl}-4(amino)phenol and inorganic salt (208 mg, 15% in NH$_4$Cl), prepared by the procedure of Example 12, was dissolved in a minimum amount of water and passed through a Sephadex TM G-10 (Pharmacia, Inc.) desalting column (1 cm × 35 cm). The salt-free amine was eluted with water and freeze-dried (11.5 mg). The amine was dissolved in water (10 ml) and placed in a round-bottom reaction flask. Thiophosgene (0,015 ml, 10 eq) dissolved in methylene chloride (1 ml) was added. The reaction mixture was stirred at room temperature for one hour. The mixture was then washed with several portions of methylene chloride to remove excess thiophosgene and the aqueous layer freeze-dried to give the crude isothiocyanato product which was characterized by fast atom bombardment mass spectrometry. (See Table I.)

EXAMPLE 14. PREPARATION OF 2-({[BIS(CARBOXYMETHYL)]AMINO}METHYL)-4-(ACETAMIDO) PHENOL.

Deionized water (35.3 g), 35.3 g of 98% iminodiacetic acid (0.25 mole), and 29.9 g of 50% aqueous sodium hydroxide solution were weighed into a round-bottom reaction flask equipped with a water-cooled reflux condenser, mechanical stirrer, thermometer with a temperature controller, and an addition funnel. The mix was heated, with stirring, to a temperature of 55° C. Aqueous 37% formaldehyde solution (21.5 g) was placed in the addition funnel and added to the reaction flask over a 15 minute period. The reaction mixture was heated at 55° C. for approximately 45 minutes, cooled and transferred to an addition funnel. To a round-bottom flask equipped as above was added 38.7 g (0.25 mole) of 98% 4-acetamidophenol, 35.3 g of deionized water, and 12.2 g of 50% aqueous sodium hydroxide solution. The mix was heated, with stirring, to a temperature of approximately 65° C., and the formaldehyde-iminodiacetic acid adduct solution added over a 30 minute period. The reaction mixture was heated at 65° C. for an additional twelve hours and cooled. Concentrated hydrochloric acid (55.5 g) was added and the reaction mixture stirred for one hour. The solution was allowed to stand for several weeks and then the crystalline precipitate filtered, washed with deionized water and dried in a vacuum oven at 65° C. for several hours. Approximately 17.4 g. of solids were recovered. The structure was confirmed by proton NMR. (See Table I.)

EXAMPLE 15. PREPARATION OF 2-({[BIS(CARBOXYMETHYL)]AMINO}METHYL)-6-{[({[BIS (CARBOXYMETHYL)]AMINO}ETHYL)((CARBOXYMETHYL)AMINO]METHYL}-4-(ACETAMIDO)PHENOL.

Approximately 5.7 g of crude 2-oxo-1,4-piperazinediacetic acid, prepared by the procedure of Example C, and 38.6 g of deionized water were added to a beaker and mixed till dissolution of the lactam was achieved. Caustic solution (13.5 g of 50% solution of sodium hydroxide) was added while maintaining the temperature at less than 30° C. by cooling in an ice water bath. The solution was then transferred to a glass tube and immersed in a 90° C. water bath for 10 minutes and then cooled in an ice water bath. The conversion of the lactam to the trisodium salt of ethylenediaminetriacetic acid was confirmed by proton NMR. The alkaline solution was then adjusted to a pH of approximately 11.9 by the addition of hydrochloric acid. The temperature was maintained at less than 25° C. by cooling in an ice water bath. The solution was transferred to a reaction vessel and 1.5 g of aqueous 37% formaldehyde solution added dropwise over a 20 minute period. A small amount of aqueous caustic solution was also added during this time for pH adjustment. The mix was stirred for an additional hour with periodic additions of aqueous sodium hydroxide to maintain the pH between 1.0–11.5.

To a separate reaction vessel was added 1.5 g of 2-({1b is (carboxy-methyl)]amino}methyl)-4-(acetamido)-phenol prepared by the procedure of Example 12, and 2.5 g of deionized water. Aqueous 25% sodium hydroxide was added, while cooling in an ice bath, to obtain a pH of about 11. The formaldehyde adduct solution prepared above was then added over a 30 minute period to the phenolic compound at a temperature of approximately 30° C. The reaction mixture was mixed and heated for an additional 10 hours at 70° C. and then cooled. Acetone (100 g) was added to a beaker and stirred with a magnetic stirrer bar. Approximately 10 g of the crude reaction mixture was added to the acetone resulting in the precipitation of a gummy material. The acetone portion was decanted and an additional 50 g of acetone added to the material and the product titurated under acetone. The acetone layer was removed by decanting and the solids dried in a vacuum oven at 60°–65° C. for several hours. The desired product was isolated from the crude mixture by passing an aqueous solution of the solids over a Q-Sepharose ™ column and isolating the desired fraction as in Example 11. (See Table I.)

EXAMPLE U. PREPARATION OF N,N'-DI(2-HYDROXY, 5-ACETAMIDOBENZYL)ETHYLENEDIAMINE-N,N'-DIACETIC ACID. (Comparative)

Ethylenediamine-N,N'-diacetic acid (10 g, 0.056 mole), 25 g of deionized water, 7.0 g of 50% sodium hydroxide solution, and 5.0 g of methanol were added to a round-bottom reaction flask equipped with a water-cooled reflux condenser, mechanical stirrer, thermometer with a temperature controller, and an addition funnel. The reaction mixture was heated to 55° C. Aqueous 37% formaldehyde solution (9.2 g, 0.11 mole) was weighed into the addition funnel and added over a twenty minute period. The reaction mixture was heated at 55° C. for one hour and then cooled and transferred to another addition funnel. To a reaction flask, equipped as above, were added 17.2 g of 4-acetamidophenol (0.11 mole), 36 g of deionized water, 2.0 g of 50% sodium hydroxide solution, and 36 g of methanol. The mix wax heated to 65° C. and the aqueous formaldehyde/ethylenediamine-N,N'-diacetic acid adduct solution added over a one hour and fifteen minute period. The reaction mixture was heated an additional 12 hours at 64°–65° C. and then cooled. A portion of the reaction product was concentrated and the methanol removed under vacuum. The solution was adjusted to pH 1.5–2.0 with hydrochloric acid resulting in the precipitation of the acetyl product. The material was filtered, washed with deionized water, and dried in a vacuum oven at 55°–60° C. for several hours. The structure was confirmed by proton NMR.

EXAMPLE V. PREPARATION OF N,N'-DI(2-HYDROXY-5-AMINOBENZYL)ETHYLENEDIAMINE-N,N'-DIACETIC ACID, HYDROCHLORIDE. (Comparative)

To approximately 0.9 g of the product isolated in Example U were added 12.5 g of deionized water and 8 g of concentrated hydrochloric acid. The solution was heated at reflux and stirred for one hour in a round-bottom reaction flask. The volatiles were removed (in vacuo), and the amine hydrochloride product dried in a vacuum oven at 50°–60° C. for several hours. The structure was confirmed by proton NMR.

EXAMPLE W. PREPARATION OF ETHYLENEDIAMINEDI(2-HYDROXY-5ACETAMIDOPHENYL)ACETIC ACID]. (Comparative)

Aqueous (50%) glyoxylic acid (30.0 g, 0.20 mole), 98% 4-acetamidophenol (30.9 g, 0.20 mole) and deionized water (22 g) were added to a round-bottom reaction flask equipped with a water-cooled reflux condenser, mechanical stirrer and a thermometer with a temperature controller. The flask was cooled with an ice-water bath and 19.0 g of 50% sodium hydroxide solution added slowly with stirring while maintaining the temperature below 30° C. Ethylenediamine (6.1 g, 0.10 mole) was added at a temperature less than 30° C. The ice bath was removed and the reaction mixture heated and stirred for five hours at 85°–86° C. Approximately 20 g of the aqueous reaction product was treated with 10 g of ethyl ether. The ether layer was removed and the procedure repeated again. The aqueous portion was then adjusted to a pH of approximately 4.2 with hydrochloric acid and agitated with 35 g of acetone. The acetone layer was removed and discarded. To the remaining material was added 65 g of methanol with stirring. The resulting solids were filtered and dried in a vacuum oven at 55°–60° C. for several hours.

EXAMPLE X. PREPARATION OF ETHYLENEDIAMINEDI[(2-HYDROXY-5AMINOPHENYL)ACETIC ACID] (Comparative)

To approximately 4.5 g of the above solids were added 6 g of deionized water and 21 g of concentrated hydrochloric acid. The mix was filtred and 6 g of water added. The solution was placed in a round-bottom reaction flask equipped with a water-cooled reflux condenser, mechanical stirrer, and a thermometer. The solution was heated for one hour at 100°–103° C. and then cooled. The volatiles were removed in vacuo and the product, the hydrochloride of ethylenediaminedi(2-hydroxy-5aminophenyl)acetic acid, was dried in a vacuum oven at 60° C. for several hours. Hydrolysis of the acetyl functionality was followed by proton NMR.

COMPLEX PREPARATION AND PERCENT COMPLEX DETERMINATION.

In the following examples the following terms were used: conc. means concentrated; OAc means the acetate moiety, OCOCH$_3$; TLC means thin layer chromatography; ambient temperature means room temperature or about 20° to 25° C.; overnight means from about 9 to 18 hours; SP-Sephadex ™ C-25 resin is a cation exchange resin having sulfonic acid functionality, sold by Pharmacia, Inc.

The yttrium and/or samarium complexes of several of the compounds were prepared and percent complexation determined as follows:

Yttrium Complex Preparation:

Complexes were made by preparing a 0.0003M yttrium solution in water. ($YCl_3 \cdot 6H_2O$, 303.26 g/mole; $Y(OAc)_3$, 12.1% $H_2O$). Radioactive $YCl_3$ (Oakridge National Laboratories) was added to give the desired number of counts. Ten µl of ligand solution (at 0.03M) were added to 990 µl of the Y solution, giving a ligand-to-metal ratio of 1:1. (Ten times the amount of ligand solution was used for a 10:1 ligand to metal ratio.) The pH was then adjusted to 7.4 using microliter quantities of hydrochloric acid or sodium hydroxide. The solution was then tested for the amount of complexed yttrium using the cation exchange method given below.

Percent Complex Determination:

A disposable 10 ml plastic (Biorad) column was filled with 1 to 2 ml of water-swelled Sephadex ™ C-25 cation exchange resin. The water was pressure eluted to the top of the resin. Fifteen µl of the complex (or more if counts were low) were added to the top of the resin. This was followed by 2 ml of 4:1 (V:V) isotonic saline:-conc. ammonium hydroxide solution as an eluent which was allowed to drip into a counting tube. This was also pressure eluted to the top of the resin. An additional 2 ml of the eluent were added and the column pressure eluted to remove all liquid. The dried resin was then placed in a third counting tube and the three tubes counted on a NaI well counter using a Canberra multichannel analyzer linked to a computer. The percent complex was determined by dividing the number of counts in the two elutions by the total counts in the elutions plus the column, all times 100. By this method, uncomplexed yttrium was retained on the column.

Samarium Complex Preparation/% Complex Determination:

Samarium complexes were formed as described previously for yttrium complexes except that 0.0003M samarium was prepared by dissolution of $Sm_2O_3$ (348.7 g mole) in 0.1M hydrochloric acid. Radioactive Sm-153 was obtained as a 0.0003M solution in 0.1M hydrochloric acid from the University of Missouri Research Reactor, Columbia, Mo. Percent complex determination was made in the same manner as for the yttrium complex. Results are summarized in Table II.

TABLE II

| Complex Example No. | Compound of Ex. No. | % Complex (10:1) Y | % Complex (10:1) Sm |
|---|---|---|---|
| 16 | 1 | 98 | |
| 17 | 2 | >99 | |
| 18 | 2 | | >99 |
| 19 | 3 | >99 | |
| 20 | 4 | >99 | |
| 21 | 5 | 99 | |
| 22 | 6 | | >99 |
| 23 | 7 | | 96** |
| 24 | 8 | | >99** |
| 25 | 9 | | >99 |
| 26 | 10 | 98 | |
| 27 | 11 | 99 | |
| 28 | 11 | 98* | |
| 29 | 12 | 99 | |
| 30 | 12 | | 98 |
| 31 | 12 | 98* | |
| 32 | 12 | | 98* |
| 33 | 15 | 99 | |

*Ligand/metal ratio was about 1:1;
**Ligand/metal ratio was about 50:1.

Examples I–XV and Comparative Examples A–F IN VIVO SCREENING OF BIFUNCTIONAL CHELATES.

The stability of certain rare earth chelates has been correlated with in-vivo testing in animals. For example, Rosoff, et al. in the *International Journal of Applied Radiation and Isotopes,* 14, 129–135 (1963), report on the distribution of radioactive rare earth chelates in mice for certain aminocarboxylic acids. The correlation found was that in vivo "the competition between the chelating agent and body constituents (inorganic and organic) for the rare-earth ion, determines its deposition and excretion." The strong rare-earth chelates are believed to dissociate very little and be excreted, while the weak and intermediate strength chelates dissociate more readily and thus are deposited in organs such as the liver. However, concentration of radionuclide in the liver is not always due to weak complex formation, but in some cases is due to the affinity that the metal chelate has for the liver (see Comparative Examples A & B in Table III). Compounds have, in fact, been prepared and utilized for the evaluation of liver function (Fritzberg, Alan R., Radiopharamceuticals: Progress and Clinical Perspectives A, (1986); U.S. Pat. Nos. 4,088,747 and 4,091,088 (Hunt et al.)

The biodistribution of several of the samarium and/or yttrium chelates disclosed herein was determined and the percent dose in the liver used as an in vivo screening procedure to qualitatively estimate the stability of the chelates. Chelates of NTA and EDTA are included for comparison. Also samarium was injected as samarium chloride in unchelated form.

Sprague-Dawley rats weighing from 150 to 200 g were purchased from Charles River Laboratories. These animals were placed in cages and fed water and food ad libitum. The animals were acclimated for at least five days before use. Prior to injection of complex, the animals were placed under a heat lamp (15 to 30 minutes) to dilate the tail vein. Then, the animal was placed in a restraining cage, the tail cleaned with an alcohol swipe, and the animal injected (50 to 200 µl) via the tail vein. After injection, the animal was placed in another cage for two hours after which time the animal was sacrificed by cervical dislocation. The animal was then dissected, the parts rinsed with deionized $H_2O$, patted dry, and weighed into a tared counting vial. Whatever size of injection was made, at least three standards of the same material were prepared and counted with the animal parts. Percent of dose is the number of counts in the organ divided by the number of counts in the standard times 100 (see Table III).

TABLE III

| Biology Example No. | Biodistribution Data Compound of Ex. No.* | Metal | % Injected Dose in Liver |
|---|---|---|---|
| I | 1 | Y | 0.87 |
| II | 2 | Y | 0.22 |
| III | 3 | Y | 0.22 |
| IV | 4 | Y | 1.4 |
| V | 5 | Y | 0.38 |
| VI | 6 | Sm | 0.38 |
| VII | 9 | Sm | 2.8 |
| VIII (10) | 10 | Sm | 1.3 |
| VIII (300) | 10 | Sm | 0.12 |
| VIII (10) | 10 | Y | 0.39 |
| VIII (300) | 10 | Ho | 0.26 |
| IX | 11 | Y | 0.22 |
| X | 11 | Sm | 0.33 |
| XI | 12 | Y | 0.28 |
| XII | 12 | Y | 0.18 |
| XIII | 12 | Sm | 0.35 |
| XIV | 12 | Sm | 0.26 |
| XV | 15 | Y | 0.37 |
| (A) | U (comp) | Sm | 12 |
| (B) | X (comp) | Sm | 24 |
| (C) | EDTA | Sm | 8.4 |
| (D) | EDTA | Sm | 4.4 |
| (E) | NTA | Sm | 8.6 |
| (F) | $SmCl_3$ | Sm | 39 |

*Complexes were prepared at ligand/metal ratios of 10:1 for Examples I–XI, XIII, and XV; at 1:1 for Example XII & XIV; at 5:1 for Example C; and at about 300:1 for Examples D and E.

EXAMPLES XVI & XVII.

The 1:1 complex of yttrium with 1-(p-aminobenzyl)-diethylenetriaminepentaacetic acid (ABDTPA), a well known bifunctional chelant used in the literature, and with the ligand of Example 2 (Now Ex. XVI) and Example 12 (now Ex. XVII) were prepared using the techniques described earlier. Several 100 microliter aliquots were then withdrawn into separate centrifuge tubes. Excess metal was added such that the total volume change is minimized and the time noted. One-half hour after metal addition, the percent complex was determined by the Sephadex ™ C-25 method and this was compared to the original amount of complex. The percent complex versus added metal gives an indication as to the lability of the ligand-metal complex. Results are given below and are compared to the EDTA-yttrium complex.

TABLE IV

| Metal/Ligand Molar Ratio | Complex Study % Complex | | | |
|---|---|---|---|---|
| | Ex. XVI | Ex. XVII | ABDTPA | EDTA |
| 1 | 99 | 95 | 97 | 98 |
| 10 | 94 | 93 | 95 | 86 |
| 100 | 84 | 90 | 92 | 78 |
| 250 | — | 90 | 87 | 48 |
| 500 | 75 | 79 | 70 | 16 |

EXAMPLE XVIII.

A 0.18M/L solution of 1-(p-aminobenzyl)diethylene-triaminepentaacetic acid (ABDTPA) and an identical 0.18M/L solution of the ligand of Example 12 were prepared in 0.5M sodium acetate buffer at pH 6.5. The solutions were then treated with 1.5 equivalents of yttrium-90 as 0.03M/L yttrium chloride. The pH of the resulting complex was 5–6. Excess Y-90 was removed by passing the complex through a one ml bed volume of Chelex ™ resin (Bio-Rad Laboratories). The concentration of the complex in this purified form was 0.0013M. An appropriate amount of the solution was added to $1.7 \times 10^{-9}$ moles of aldehyde containing CC-46 monoclonal antibody to give a 40:1 ratio of complex to antibody. After one hour exposure a 236 molar excess (over antibody) of $NaCNBH_3$ was added and the solutions allowed to set for approximately one hour. After this time the antibody (and any covalently attached complex) was separated from unbound complex by Sephadex ™ G-25 gel filtration. This procedure gave an average of 5.0 complexes per antibody for 1-(p-aminobenzyl)diethylenetriaminepentaacetic acid and an average of 5.4 complexes per antibody for the ligand of Example 12.

EXAMPLE XIX.

In order to demonstrate the inertness of the antibody-complex conjugates of Example XVIII, the conjugates were challenged with an excess of diethylenetriaminepentaacetic acid (DTPA) in the following manner. The purified antibody-complexes were added to HEPES buffer (N-2-hydroxyethylpiperazine-N'-2-ethanesulfonic acid) at pH 7.4 and treated with an appropriate amount of 0.1M DTPA solution (pH 7.4) to ensure a 1000 fold molar excess of DTPA over complex attached to antibody. After one hour an aliquot was removed and the antibody-complex conjugates were separated from low molecular weight substances using gel-filtration. The results indicate that the ABDTPA system lost over 98% of the yttrium while the system using the ligand of Example 12 lost approximately 39% of the yttrium.

EXAMPLE XX. PREPARATION OF 2,6-BIS{[(2-{BIS(CARBOXYMETHYL)-]AMINO}ETHYL) (CARBOXYMETHYL)]AMINOMETHYL}-4-(AMINO)PHENOL, SAMARIUM COMPLEX

A samarium solution was prepared by combining in a 1 ml vial radioactive $^{153}Sm$ (200 μof a $3 \times 10^{-4}M$ solution in 0.1M hydrochloric acid, $6 \times 10^{-5}$ mmole) and "cold" $SmCl_3.6H_2O$ (4.8 mg, $1.31 \times 10^{-2}$ mmole). This solution was added to 2,6-bis{[(2-{[bis(carboxymethyl)-]amino}ethyl) (carboxymethyl)]aminomethyl}-4-(acetamido)phenol (3.2 mg, $5.31 \times 10^{-3}$ mmole), prepared by the procedure of Example 11. The pH was then adjusted to 7 by the addition of sodium hydroxide (40 ul of a 1.0M solution). The percent complex was determined to be 68% using the Sephadex ™ C-25 method.

The above complex was purified by anion exchange chromatography (Q-Sepharose ™, 1.5 cm ×21 cm, 0 to 1M NaCl over 30 min, 2 ml/min, detection at 285 nm). Complex-containing fractions (1 ml each, 6 ml total) were combined and the percent complex was determined to be 95%.

EXAMPLE XXI. CONJUGATION OF 2,6-BIS{[(2-{BIS(CARBOXYMETHYL)-]AMINO}ETHYL) (CARBOXYMETHYL)]AMINOMETHYL}-4-(AMINO)PHENOL, SAMARIUM COMPLEX TO CC-46 MONOCLONAL ANTIBODY

Sodium bicarbonate (60 mg, $7.14 \times 10^{-1}$ mmole) was placed in a one dram glass vial and the complex solution from Example XX was added (1 ml, about $8.8 \times 10^{-4}$ mmole). Thiophosgene (10 μl, $1.31 \times 10^{-1}$ mmole) in chloroform (1 ml) was added and the vial was sealed.

The mixture was shaken for 15 minutes, after which the aqueous layer was washed twice with chloroform (1 ml portions). Percent complex was checked and found to be 96%.

The above isothiocyanate Sm complex (100 μl, about $8.8 \times 10^{-5}$ mmole) was combined with CC-46 monoclonal antibody (100 μl of an 8 mg/ml solution, about $5.3 \times 10^{-6}$ mmole) and allowed to stand for 24 hours. The amount of complex conjugated to antibody was determined to be 46% by size exclusion chromatography.

EXAMPLE XXII. PREPARATION OF 2-[BIS(2-{[(BIS(CARBOXYMETHYL)] AMINO}ETHYL)AMINO]-2-[5-AMINO-2-(CARBOXYMETHYLOXY) PHENYL]ETHANOIC ACID AND 2-[{2-[(2{[BIS(CARBOXYMETHYL)-]AMINO}ETHYL) (CARBOXYMETHYL)AMINO]ETHYL}(CARBOXYMETHYL)AMINO]-2-[5-AMINO-2-(CARBOXYMETHYLOXY)PHENYL]ETHANOIC ACID, SAMARIUM COMPLEX

A solution of the ligands from Example 7 was prepared by dissolving 266 mg of the lyophilized solid in 1 ml of water. A 33.85 μl aliquot of this solution was treated with 1 ml of $3 \times 10^{-4}$M SmCl$_3$ in 0.1N hydrochloric acid containing a tracer amount of radioactive $^{153}$Sm. The pH of the complex solution was adjusted to about 13 using 50 weight % sodium hydroxide and then adjusted to about pH 7.5 using 1.0N hydrochloric acid. The percent Sm that was complexed was determined as described in Examples 16 through 33 and was found to be 100%.

The inertness of the complex was demonstrated by placing two 500 μl aliquots of the complex solution in separate vials. One portion was treated with 1-2 μl portions of 0.1N hydrochloric acid until the pH was lowered and the other portion was treated with 0.1N sodium hydroxide to bring the pH up. The complexes were allowed to set for 5-10 minutes at each pH change, then they were sampled to determine the percent complexation at that pH by the method described for Examples 16 through 33. The results are shown in the following table.

TABLE V

| pH | % Complexed |
|----|-------------|
| 1  | 98          |
| 2  | 100         |
| 3  | 100         |
| 4  | 100         |
| 5  | 100         |
| 7  | 100         |
| 9  | 100         |
| 11 | 100         |
| 13 | 100         |

EXAMPLE XXIII. PREPARATION OF 2-[{2-[(2{[BIS(CARBOXYMETHYL)]AMINO}ETHYL) (CARBOXYMETHYL) AMINO]ETHYL} (CARBOXYMETHYL) AMINO]-2-[5-AMINO-2-(CARBOXYMETHYLOXY)PHENYL]ETHANOIC ACID, SAMARIUM COMPLEX

A solution of the ligand from Example 8 was prepared by dissolving 13.9 mg of the brownish solid in 772 μl of water. A complex was prepared by dissolving 500 of this ligand solution in 1 ml of $3 \times 10^{-4}$M SmCl$_3$ (containing 0.1N hydrochloric acid) that had been spiked with radioactive $^{153}$Sm. The pH of the complex solution was adjusted to about 7 by the addition of 1.0N sodium hydroxide. The percent complexation was determined by the method described for Examples 16 through 33 and found to be 96 %.

The inertness of the complex was demonstrated by placing two 500 μl aliquots of the complex solution in separate vials. One portion was treated with 1-2 μportions of 1.0N hydrochloric acid until the pH was lowered and the other portion was treated with 0.1N, 1.0N and 50 weight % sodium hydroxide to bring the pH up. The complexes were allowed to set for about 5 minutes at each pH change, then they were sampled to determine the percent complexation at that pH by the method described for Examples 16 through 33. The results are shown in the following table.

TABLE VI

| pH | % Complexed |
|----|-------------|
| 1  | 91          |
| 2  | 88          |
| 3  | 92          |
| 5  | 96          |
| 7  | 96          |
| 9  | 99          |
| 12 | 98          |
| 13 | 99          |

EXAMPLES OF BIODISTRIBUTION DATA

Complexes were prepared by mixing a solution of ligand and metal then adjusting the pH to 7-8. The amount of metal that was complexed to ligand was determined by cation exchange chromatography. Free metal was retained by the resin, metal in the form of a complex was not.

One-hundred μl of the complexes were injected into the tail vein of three Sprague Dawley rats. Two hours after injection, the rats were killed by cervical dislocation and samples of tissues were taken. The tissues were weighed and the amount of radiation in each tissue determined by measuring the number of counts using a NaI well counter and comparing them to standards. The % dose in blood was determined assuming that the weight of blood was 6.5% of the animal weight. Muscle was calculated using 46% of body weight. The amount in bone was 25 times the % dose in a femur. The examples below differ in the ligand, amount of ligand and amount of metal used. Non-radioactive metal was used to obtain the desired ligand to metal ratios and tracer radioactive metal was used to obtain the biodistribution.

EXAMPLE XXIV.

The ligand of Example 10 was mixed with a Sm-153 solution. The concentration of Sm was $3 \times 10^{-4}$M and the ligand was used with a 300 times molar excess. The biodistribution showed 52.7% in the bone, 0.12% in the liver, 0.005% in the spleen, 0.23% in the muscle, and 0.05% in the blood.

EXAMPLE XXV.

The ligand of Example 10 was complexed to Ho-166. The concentration of Ho was 3X10-4M and the formulation contained 300 times molar excess ligand. The biodistribution showed 52.9% in the bone, 0.26% in the liver, 0.007% in the spleen, 1.1% in the muscle, and 0.09% in the blood.

EXAMPLE XXVI.

The ligand of Example 10 was complexed to Sm-153 using a concentration of Sm of $3 \times 10^{-4}$M and 10 times molar excess ligand. The biodistribution showed 48.5% in the bone, 1.3% in the liver, 0.01% in the spleen, 0.73% in the muscle and 0.18% in the blood.

EXAMPLE XXVII.

A rabbit was injected in the same manner as the rats with a formulation having Y-90 with Y at $3 \times 10^{-4}$M and the ligand of Example 10 at 10 times molar excess. The activity was found to concentrate in bone (59%) with liver (1.1%), spleen (0.19%), muscle (1.5%) and blood (0.68%) showing minimal uptake.

EXAMPLE XXVIII.

The ligand of Example 1 was complexed using Y-90 as a tracer. The Y concentration was $3 \times 10^{-4}$M and the ligand was added in a 10 times molar excess. The rat biodistribution (average of two rats) showed 56.1% in the bone, 0.87% in the liver, 0.03% in the spleen, 0.78% in the muscle, and 0.57% in the blood.

EXAMPLE XXIX

A dog was presented with an osteosarcoma in the right proximal humerus and walked with significant lameness. A complex was prepared using the ligand of Example 10 with a Sm-153 solution. The concentration of Sm was $3 \times 10^{-4}$M and the ligand was used with a 300 times molar excess. The specific activity of the Sm-153 was 30 mCi/ml. The dog was given an I.V. injection of this complex containing 0.95 mCi of Sm-153 per Kg body weight of the dog. One week after injection the dog's gait was noticeably improved.

TABLE 1

GENERIC STRUCTURE (I)

| Example No. | Z | X | R$_5$ | n | R$_1$ | R$_2$ | R$_3$ | R$_4$ | B |
|---|---|---|---|---|---|---|---|---|---|
| 1 | —NHCOCH$_3$ | —H | —H | 0 | — | — | —H | —COOH | —NH—CH$_2$—N(CH$_2$COOH)$_2$ |
| 2 | —NHCOCH$_3$ | CH$_2$COOH | —H | 0 | — | — | —H | —COOH | —N(CH$_2$COOH)—CH$_2$—N(CH$_2$COOH)$_2$ |
| 3 | —NH$_2$ | CH$_2$COOH | —H | 0 | — | — | —H | —COOH | —N(CH$_2$COOH)—CH$_2$—N(CH$_2$COOH)$_2$ |
| 4 | —NHCOCH$_3$ | —H | —H | 0 | — | — | —H | —COOH | —N(CH$_2$CN)—CH$_2$—N(CH$_2$COOH)$_2$ |
| 5 | —NH$_2$ | —H | H | 0 | — | — | —H | —COOH | —N(CH$_2$COOH)—CH$_2$—N(CH$_2$COOH)$_2$ |
| 6 | —NHCOCH$_3$ | CH$_2$CO$_2$H | H | 0 | — | — | —H | —COOH | —N(CH$_2$COOH)CH$_2$CH$_2$N(CH$_2$COOH)CH$_2$CH$_2$N(CH$_2$COOH)$_2$ |

TABLE 1-continued
GENERIC STRUCTURE
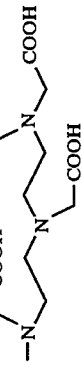
| Example No. | Z | X | R₅ | n | R₁ | R₂ | R₃ | R₄ | B |
|---|---|---|---|---|---|---|---|---|---|
| 7 | —NH₂ | CH₂COOH | H | 0 | — | — | —H | —COOH | 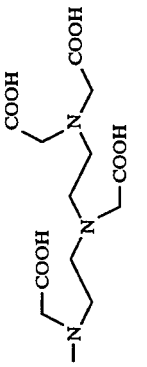 |
| 8 | —NH₂ | CH₂COOH | H | 0 | — | — | —H | —COOH | 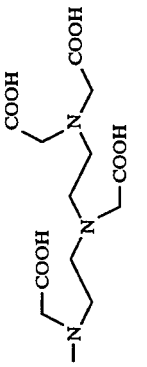 |
| 9 | —NHCOCH₃ | CH₂CO₂H | —H | 0 | — | — | —H | —COOH | 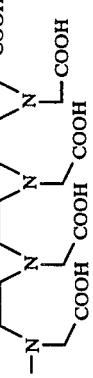 |

TABLE 1-continued
GENERIC STRUCTURE (I)
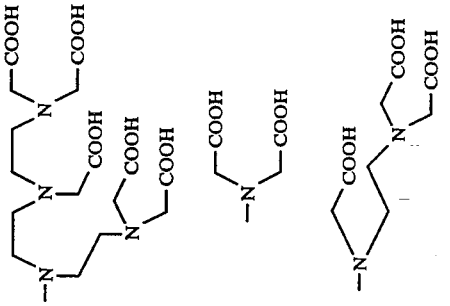
| Example No. | Z | X | R5 | n | R1 | R2 | R3 | R4 | B |
|---|---|---|---|---|---|---|---|---|---|
| 10 | —NHCOCH3 | —H | (structure) | 0 | — | — | —H | —COOH | (structure) |
| 11 | —NHCOCH3 | —H | (structure) | 0 | — | — | —H | —H | (structure) |
| 12 | —NH2 | —H | (structure) | 0 | — | — | —H | —H | (structure) |
| 13 | —NCS | —H | (structure) | 0 | — | — | —H | —H | (structure) |
| 14 | —NHCOCH3 | —H | —H | 0 | — | — | —H | —H | (structure) |

TABLE 1-continued
GENERIC STRUCTURE
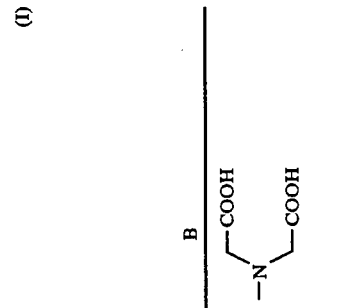
(I)
| Example No. | Z | X | R5 | n | R1 | R2 | R3 | R4 | B |
|---|---|---|---|---|---|---|---|---|---|
| 15 | —NHCOCH3 | —H | HOOC—CH2\\N—CH2—N/—CH2COOH \\CH2COOH | 0 | — | — | —H | —H | —N(CH2COOH)2 |

What we claim is:

1. A complex comprising a chelant possessing ortho ligating functionality having the formula

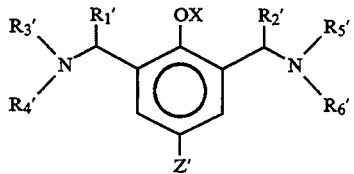

wherein Z' is selected from the group consisting of hydrogen, $NH_2$, $NO_2$, $NHC(O)CH_3$ or $N(R')_2$, where R' is hydrogen and $C_1$–$C_3$ alkyl;

X is selected from the group consisting of hydrogen, $C_1$–$C_3$ alkyl and $CR_3R_4COOH$;

$R_3$ and $R_4$ are independently selected from the group consisting of hydrogen, $C_1$–$C_3$ alkyl and COOH;

$R'_1$ and $R'_2$ each are independently selected from the group consisting of hydrogen and COOH, with the proviso that at least one is COOH;

$R'_3$, $R'_4$, $R'_5$ and $R'_6$ are independently selected from the group consisting of hydrogen and $CR_3R_4COOH$, with the proviso that at least three are $CR_3R_4COOH$; or a pharmaceutically acceptable salt thereof; and complexed with a radionuclide metal ion selected from the group consisting of $^{153}Sm$, $^{166}Ho$, $^{90}y$, $^{149}pm$, $^{159}Gd$, $^{0}La$, $^{177}Lu$, $^{175}Yb$, $^{47}Sc$ and $^{142}Pr$.

2. The chelant of claim 1 wherein $R'_1$ and $R'_2$ are COOH, $R'_3$, $R'_4$, $R'_5$ and $R'_6$ are $CH_2COOH$.

3. The chelant of claim 1 wherein Z' is $NHC(O)CH_3$ and X is hydrogen.

4. A complex of claim 1 wherein the metal ion is $^{153}Sm$, $^{166}Ho$, $^{90}y$, $^{159}Gd$, $^{177}Lu$ or $^{175}Yb$.

5. A complex of claim 27 wherein the metal ion is $^{153}Sm$, $^{166}Ho$, $^{90}y$, $^{159}Gd$ or $^{177}Lu$.

6. A therapeutically effective formulation comprising the complex of claim 1 or a physiologically acceptable salt thereof, and a physiologically acceptable carrier.

7. A method for the therapeutic treatment of an animal having one or more calcific tumors which comprises administering to said animal a therapeutically effective amount of a formulation of claim 6.

8. A method for the therapeutic treatment of an animal having bone pain which comprises administering to said animal a therapeutically effective amount of a formulation of claim 6.

* * * * *

UNITED STATES PATENT AND TRADEMARK OFFICE
CERTIFICATE OF CORRECTION

PATENT NO. : 5,342,604
DATED : August 30, 1994
INVENTOR(S) : David A. Wilson et al.

It is certified that error appears in the above-indentified patent and that said Letters Patent is hereby corrected as shown below:

column 42, line 6, "$^0$La" should read -- $^{140}$La --.

column 42, line 13, "claim 27" should read -- claim 2 --.

Signed and Sealed this

Second Day of May, 1995

Attest:

BRUCE LEHMAN

*Attesting Officer*  *Commissioner of Patents and Trademarks*